(12) United States Patent
Johnson et al.

(10) Patent No.: US 6,852,291 B1
(45) Date of Patent: Feb. 8, 2005

(54) HYBRID VALVE APPARATUS AND METHOD FOR FLUID HANDLING

(75) Inventors: James E. Johnson, Sebastopol, CA (US); Neil R. Picha, Petaluma, CA (US); Mitchel J. Doktycz, Knoxville, TN (US)

(73) Assignee: Innovadyne Technologies, Inc., Rohnert Park, CA (US)

( * ) Notice: Subject to any disclaimer, the term of this patent is extended or adjusted under 35 U.S.C. 154(b) by 311 days.

(21) Appl. No.: 09/689,548

(22) Filed: Oct. 11, 2000

(51) Int. Cl.[7] .............................. B01L 3/02; G01N 1/10; E03B 11/01; E03C 1/18
(52) U.S. Cl. ........................ 422/103; 422/100; 436/180; 137/597; 137/625.46
(58) Field of Search ................................ 422/100, 103; 137/597, 625.46; 222/144

(56) References Cited

U.S. PATENT DOCUMENTS

| | | | | | |
|---|---|---|---|---|---|
| 3,405,734 | A | * | 10/1968 | Smit et al. ............. | 137/625.46 |
| 3,645,142 | A | * | 2/1972 | Turpin ..................... | 73/864.12 |
| 3,747,630 | A | * | 7/1973 | Hurrell ........................ | 137/312 |
| 3,868,970 | A | * | 3/1975 | Ayers et al. ............ | 137/625.46 |
| 3,963,148 | A | * | 6/1976 | Proni et al. ................. | 222/132 |
| 4,013,413 | A | * | 3/1977 | Stewart et al. ................ | 436/53 |
| 4,120,661 | A | * | 10/1978 | Naono ......................... | 422/100 |

(List continued on next page.)

FOREIGN PATENT DOCUMENTS

| EP | 1197693 A2 | 4/2002 |
|---|---|---|
| WO | WO 97/26539 | 7/1997 |
| WO | WO 99/42752 | 8/1999 |
| WO | WO 00/51736 | 8/2000 |
| WO | WO 01/04909 | 1/2001 |
| WO | WO 01/28701 | 4/2001 |
| WO | WO 01/65214 | 9/2001 |

OTHER PUBLICATIONS

Hue P. Le, *Progress and Trends in Ink–jet Printing Technology*, Journal Of Imaging Science And Technology, vol. 42, No. 1, Jan./Feb. 1998, pp 49–62.
Ilene Schneider, *Instrumentation—Doing More With Less—Discover the turnkey systems now streamlining the entire liquid handling process*, Sep. 2002—Genomics & Proteomics.
Patent Abstracts of Japan, Publication No. 63295267, *Recovering Method For Ink Jet Recorder*, Moriyama Jiro, filed May 27, 1987.

*Primary Examiner*—Jill Warden
*Assistant Examiner*—Brian R. Gordon
(74) *Attorney, Agent, or Firm*—Beyer Weaver & Thomas LLP

(57) ABSTRACT

A hybrid valve apparatus for use with an aspiration actuator and a dispensing actuator to transfer fluid from a reservoir to a test site on a substrate surface. The hybrid valve includes a valve assembly movable between an aspiration condition and a dispensing condition, and a manifold device coupled to the valve assembly. The manifold device includes a fluid aspiration conduit having a first aspiration port in fluid communication with the aspiration actuator. On an opposite end of the aspiration conduit is a second aspiration port in selective fluid communication with the valve assembly to selectively aspirate a liquid sample slug from the reservoir into a discrete sample path when the valve assembly is in the aspiration condition. The manifold device further includes a fluid dispensing conduit having a first dispensing port in fluid communication with the dispensing actuator, and a second dispensing port in selective fluid communication with the valve assembly. When the valve assembly is in the dispensing condition, the sample path is fluidly coupled to the dispensing actuator to selectively dispense at least one droplet of the liquid sample slug therefrom, while simultaneously being out of fluid communication with the aspiration actuator. In contrast, in the aspiration condition, the sample path is in fluid communication with the aspiration actuator, while being out of fluid communication with the dispensing actuator.

43 Claims, 17 Drawing Sheets

U.S. PATENT DOCUMENTS

| | | | | |
|---|---|---|---|---|
| 4,369,664 A | * | 1/1983 | Bunce et al. | 73/864.12 |
| 4,459,267 A | * | 7/1984 | Bunce et al. | 422/100 |
| 4,461,328 A | * | 7/1984 | Kenney | 141/67 |
| 4,625,569 A | | 12/1986 | Toei et al. | |
| 4,694,861 A | * | 9/1987 | Goodale et al. | 137/624.19 |
| 4,702,889 A | * | 10/1987 | Cabrera et al. | 422/103 |
| 4,705,627 A | * | 11/1987 | Miwa et al. | 210/264 |
| 4,726,932 A | * | 2/1988 | Feier et al. | 422/103 |
| 4,818,706 A | * | 4/1989 | Starr | 436/180 |
| 4,948,565 A | * | 8/1990 | Bemis et al. | 422/103 |
| 5,207,109 A | | 5/1993 | Olsen | |
| 5,250,263 A | * | 10/1993 | Manz | 422/81 |
| 5,312,757 A | | 5/1994 | Matsuyama et al. | |
| 5,405,585 A | * | 4/1995 | Coassin | 422/100 |
| 5,525,515 A | | 6/1996 | Blattner | |
| 5,578,275 A | * | 11/1996 | Rosenberg et al. | 422/163 |
| 5,601,115 A | * | 2/1997 | Broerman | 137/595 |
| 5,738,728 A | | 4/1998 | Tisone | |
| 5,741,554 A | | 4/1998 | Tisone | |
| 5,743,960 A | | 4/1998 | Tisone | |
| 5,820,824 A | * | 10/1998 | Tanaka | 422/100 |
| 5,833,925 A | * | 11/1998 | Shu et al. | 422/63 |
| 5,849,598 A | * | 12/1998 | Wilson et al. | 436/180 |
| 5,916,524 A | | 6/1999 | Tisone | |
| 5,985,214 A | | 11/1999 | Stylli et al. | |
| 6,033,911 A | * | 3/2000 | Schultz et al. | 436/49 |
| 6,040,186 A | * | 3/2000 | Lewis et al. | 436/53 |
| 6,063,339 A | | 5/2000 | Tisone et al. | |
| 6,066,298 A | * | 5/2000 | Fukunaga | 422/100 |
| 6,083,763 A | | 7/2000 | Balch | |
| 6,096,276 A | * | 8/2000 | Laursen | 422/103 |
| 6,112,605 A | | 9/2000 | Papen et al. | |
| 6,158,269 A | * | 12/2000 | Dorenkott et al. | 73/37 |
| 6,322,752 B1 | * | 11/2001 | Siddiqui et al. | 422/100 |
| 6,378,556 B1 | * | 4/2002 | Fondse | 137/625.48 |
| 6,447,678 B2 | * | 9/2002 | Chau | 210/266 |
| 2001/0026772 A1 | * | 10/2001 | Fuerst et al. | 422/64 |
| 2001/0053337 A1 | * | 12/2001 | Doktycz et al. | 422/100 |
| 2001/0055545 A1 | * | 12/2001 | Takii et al. | 422/100 |
| 2002/0192113 A1 | * | 12/2002 | Uffenheimer et al. | 422/67 |
| 2003/0021734 A1 | * | 1/2003 | Vann et al. | 422/100 |

* cited by examiner

ASPIRATE POSITION

DISPENSE POSITION

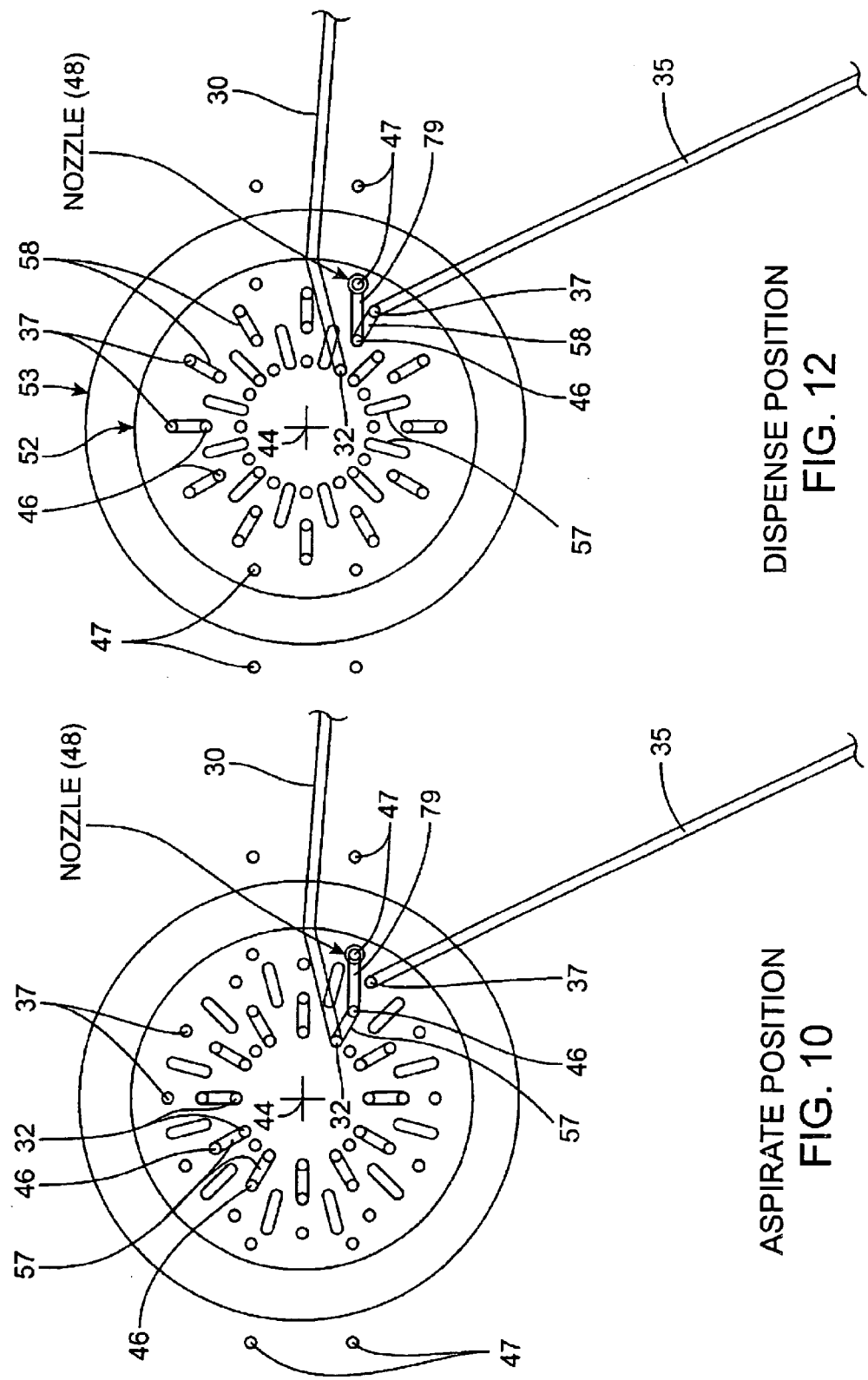

FIG. 16 DISPENSE POSITION

ASPIRATE POSITION

DISPENSE POSITION

HYBRID VALVE APPARATUS AND METHOD FOR FLUID HANDLING

TECHNICAL FIELD

The present invention relates to fabrication, apparatus, system and methods for manipulating arrays of samples, reagents or solvents from a source or reservoir to a destination substrate, and more particularly, relates to a hybrid valve system applied to aspirate, dispense and switch fluids during large-scale chemical or biochemical screening assays, syntheses, arraying and plate spotting.

BACKGROUND ART

Advances in Life Sciences, particularly in genomics and proteomics, have greatly increased the potential number of reactions and analyses that must be performed by the biotechnology and pharmaceutical industries. An estimated 30 million tests are required to screen a typical pharmaceutical company's compound library against target receptors. The typical number of tests will increase dramatically as information is gleaned from the sequencing of the human genome. To meet these increasing throughput demands in an economically feasible manner, miniaturization of tests is imperative.

Technological advances are enabling the demonstration and use of microscale chemical/biochemical reactions for performing various types of analyses. Implementation of these reactions at such smaller scales offer economies that are unmatched by conventional approaches. Reduced volumes can lower costs by an order of magnitude but conventional liquid-handling devices fail at the required volumes. Parallel implementation provides even greater advantages as demonstrated by the use of high-density plates for screening and high-density MALDI-TOF plates for mass spectrometry analyses of proteins. The rate-limiting hardware is low volume liquid transfer technology that is robust and scalable for compounds of interest. With growing demand, the development of fluid handling devices adept at manipulating sub-microliter volumes of multiple reagents, is needed.

Current systems for handling liquid reagents often employ a "pick and place" technique where a sample from a source plate, usually a microtiter plate, is picked up and placed into another reservoir known as the target plate. This technique is often applied for replicating plates, where scale reduction between the source and the target plates are beneficially realized. Typically, an appropriate volume is aspirated from a source plate and deposited to a target site on a multiple target plate. In this arrangement, reduced sample volumes and sample spacing are required for higher degrees of miniaturization.

In other advancements using "pick and place" distribution, drop-on demand ink jet technology has been adopted for accurately delivering volumes on the order of picoliters. This technology is not only capable of volumetric precision, by but also positional accuracy as well. These ink jet systems typically employ thermal, piezoelectric, or solenoid actuation to deliver defined volumes of liquid sample to precise locations, increasing test site array density.

Two of these approaches, in particular, thermal and piezoelectric ink jet technology, utilize micromachined actuation mechanisms and dispensing orifices which offer non-contact dispensing from the tip without requiring capillary contact for flow purposes. Problematic to these devices is plugging of orifices and scalability. While this printing technology is capable of low-volume, accurate delivery, the initial systems for dispensing chemical reagents lack speed and efficiency due to conventional switching technology. A syringe drive per channel is generally employed, limiting systems to a scale that fails to provide the required throughput. The current systems are unable to quickly switch multiple channels between large-scale metering tasks and subsequent micro dispensing tasks, failing to exploit the advantages and the high speed afforded by this non-contact printing technology.

DISCLOSURE OF INVENTION

The present invention provides a hybrid valve apparatus for use with an aspiration actuator and a dispensing actuator to transfer fluid from a reservoir to a test site on a substrate surface. The hybrid valve includes a valve assembly movable between an aspiration condition and a dispensing condition, and a manifold device coupled to the valve assembly. The manifold device includes a fluid aspiration conduit having a first aspiration port in fluid communication with the aspiration actuator. On an opposite end of the aspiration conduit is a second aspiration port in selective fluid communication with the valve assembly to selectively aspirate a liquid sample slug from the reservoir into a discrete sample path when the valve assembly is in the aspiration condition. The manifold device further includes a fluid dispensing conduit having a first dispensing port in fluid communication with the dispensing actuator, and a second dispensing port in selective fluid communication with the valve assembly. When the valve assembly is in the dispensing condition, the sample path is fluidly coupled to the dispensing actuator to selectively dispense at least one droplet of the liquid sample slug therefrom, while simultaneously being out of fluid communication with the aspiration actuator. In contrast, in the aspiration condition, the sample path is in fluid communication with the aspiration actuator, while being out of fluid communication with the dispensing actuator.

In one embodiment, the hybrid valve includes a plurality of aspiration actuators and a plurality of dispensing actuators to transfer fluid from a plurality of fluid reservoirs to a plurality of test sites on the substrate surface. The manifold device defines a plurality of independent fluid aspiration conduits, each of which includes a first aspiration port in fluid communication with a corresponding one of the plurality of aspiration actuators, and a second aspiration port terminating at a stator face of the manifold for selective fluid communication with the valve assembly. Thus, when the valve assembly is in the aspiration condition, each aspiration actuator can be operated to selectively aspirate a respective liquid sample slug from a corresponding reservoir of sample fluid into discrete sample paths. The manifold device further defines a plurality of fluid dispensing conduits, each having a respective first dispensing port in fluid communication with a corresponding one of the plurality of dispensing actuators, and a second dispensing port terminating at the stator face. When the valve assembly is in the dispensing condition, each dispensing actuator can be operated to selectively dispense at least one droplet of the corresponding liquid sample slug from the corresponding sample path.

Accordingly, at no time are the aspiration actuator or the dispensing actuator both in fluid communication with the sample path when the valve assembly is in either the aspiration or dispensing condition. This arrangement is highly beneficial in that contamination of the dispensing actuators can be eliminated by isolating the aspiration paths and dispensing actuators. Moreover, each fluid path is operatively switched between the aspiration actuator and the dispensing actuator enabling the use of conventional liquid handling techniques, such as air gaps, to isolate system hydraulic fluid during aspiration, and the subsequent low-volume, non-contact dispensing of the reagents or sample fluid to the test site.

In the preferred embodiment, the manifold device includes a stator face configured for rotational sliding contact with a rotor face of the valve assembly at a rotor-stator interface. Each of the second aspiration ports and the second dispensing ports terminate at the stator face for communication with the valve assembly. The manifold device further includes a plurality of primary passages each defining at least a portion of their respective sample paths. Each primary passage has a upper communication port which also terminates at the stator face. The upper communication port remains in fluid communication with the respective sample channel when in the aspiration condition and the dispensing condition. Thus, the primary passage is fluidly coupled to the respective aspiration actuator in the aspiration condition, and fluidly coupled to the respective dispensing actuator in the dispensing condition.

The hybrid valve may include a plurality of removable nozzle members mounted to the manifold device to dispense the respective droplet. Each nozzle includes one end fluidly coupled to a corresponding primary passage and an opposite end terminating at a dispensing orifice.

In another aspect of the present invention, the manifold device may be provided by a plurality of laminated plate members which collectively define the body of the manifold. At least two plate members are fixedly mounted together in a manner cooperatively defining at least one of the aspiration conduits and the dispensing conduits. The two plate members include a first plate member having a first interface surface and a second plate member having an opposed second interface surface fixedly joined therebetween at a first interface. This first interface surface defines a plurality of first grooves which cooperate with the second interface surface of the second plate member to define at least the aspiration conduits or the dispensing conduits.

The dispensing actuators may include drop-on demand ink-jet printing valving in the form of a thermal ink-jet valve, a solenoid ink-jet valve, or a piezoelectric ink-jet valve. The aspiration actuators, on the other hand, may include a syringe-type metering device.

In still another aspect of the present invention, a method may be provided for transferring liquid sample from a fluid reservoir to a test site on a target substrate. The method includes providing a fluid manifold device defining a fluid aspiration conduit having a first aspiration port in fluid communication with an aspiration actuator and a second aspiration port in fluid communication with the valve assembly. The manifold device further defines a fluid dispensing conduit having a first dispensing port in fluid communication with the dispensing actuator and a second dispensing port in fluid communication with the valve assembly. The method includes positioning the valve assembly in an aspiration condition, fluidly coupling the aspiration actuator to a discrete sample path, and fluidly decoupling the dispensing actuator from the sample path; and actuating the aspiration actuator to aspirate a liquid sample slug from a sample reservoir into the sample path. The method further includes positioning the valve assembly in a dispensing condition, fluidly coupling the dispensing actuator to the sample path, and fluidly decoupling the aspiration actuator from the same path.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIG. 10 is an enlarged top plan view of the rotor/stator interface of FIG. 9, in the aspiration condition.

FIG. 12 is an enlarged top plan view of the rotor/stator interface of FIG. 11, in the dispensing condition.

BEST MODE OF CARRYING OUT THE INVENTION

Figure 1:
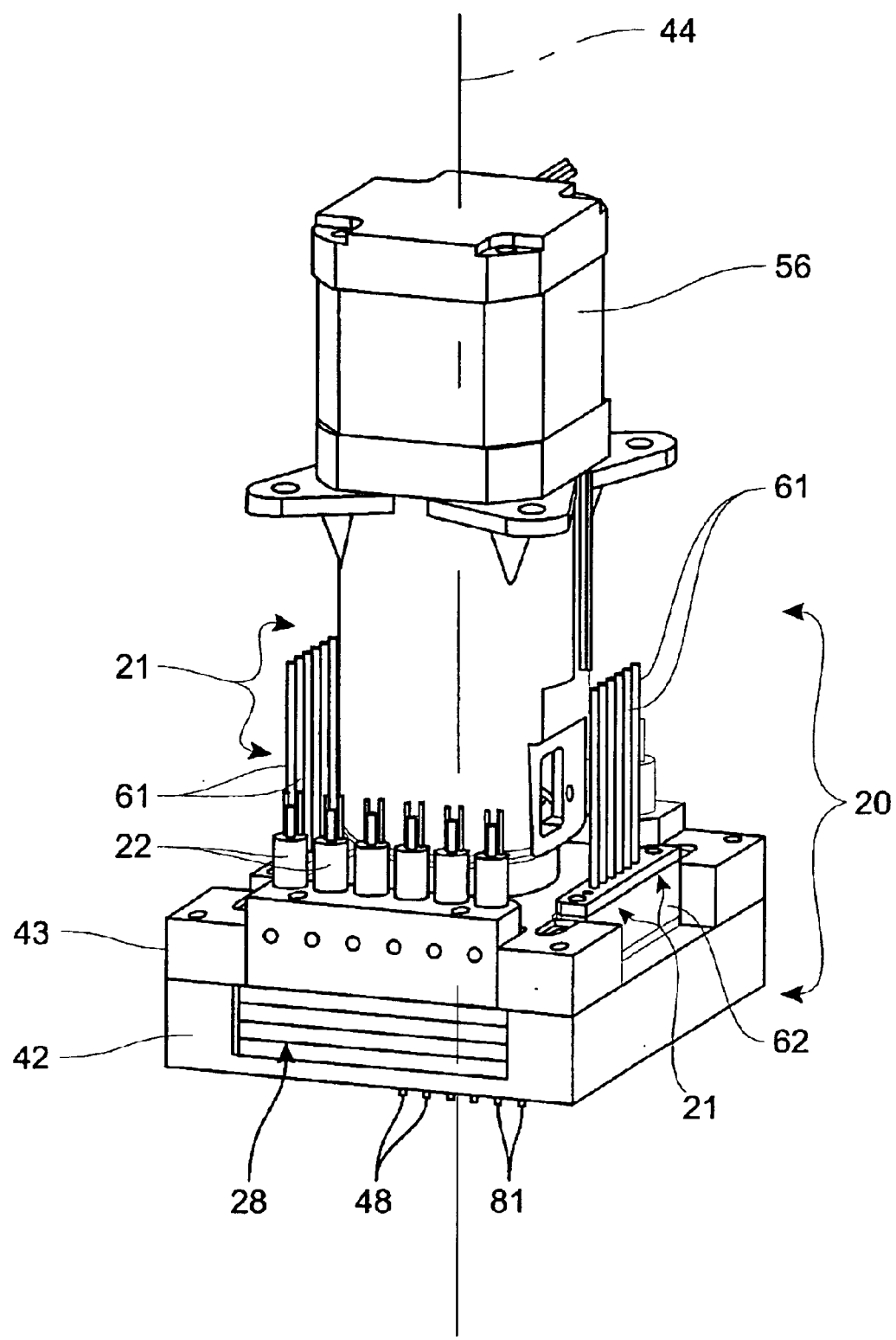
FIG. 1 is a top perspective view of the hybrid valve apparatus constructed in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Referring now to FIGS. 1–6, 15 and 16, a hybrid valve apparatus, generally designated 20, is provided for use with an aspiration source 21 and a dispensing source 22 to transfer sample or reagent fluid from a reservoir 23 to a test site 25 on a substrate surface 26. Broadly, the hybrid valve apparatus 20 includes a valve assembly 27 (FIGS. 15 and 16) movable between an aspiration condition (FIGS. 5, 9 and 10) and a dispensing condition (FIGS. 6, 11 and 12), and a manifold device 28 coupled to the valve assembly. The manifold device 28 includes a fluid aspiration conduit 30 having a first aspiration port 31 in fluid communication with the aspiration source 21. On an opposite end of the aspiration conduit 30 is a second aspiration port 32 in selective fluid communication with the valve assembly 27 to selectively aspirate a liquid sample slug from the reservoir 23 into a discrete sample path 33 when the valve assembly 27 is in the aspiration condition. The manifold device 28 further includes a fluid dispensing conduit 35 having a first dispensing port 36 in fluid communication with the dispensing source 22, and a second dispensing port 37 in selective fluid communication with the valve assembly 27. When the valve assembly 27 is oriented in the dispensing condition (FIGS. 6, 11 and 12), the sample path 33 is fluidly coupled to the dispensing source 22 to selectively dispense at least one droplet 34 of the liquid sample slug therefrom. Importantly, in this orientation, the valve assembly 27 also fluidly decouples the sample path 33 from the aspiration source 21. In contrast, in the aspiration condition (FIGS. 5, 9 and 10), the valve assembly 27 fluidly couples the sample path 33 to the aspiration source 21, while simultaneously being out of fluid communication with the dispensing source 22.

Accordingly, the hybrid valve apparatus provides a switching system which regulates fluid communication of the aspiration source, such as an aspiration actuator, and the dispensing source, such as a dispensing actuator, with the sample path containing the sample or reagent fluid. Whether the hybrid valve apparatus is in the aspiration condition or the dispensing condition, at no time will the valve assembly allow the sample path be in fluid communication with both the aspiration actuator and the dispensing actuator, simultaneously. This arrangement is beneficial in that the dispensing source can not be contaminated by the sampled fluid due to the isolating of the dispensing source from the sample path during the aspiration of the fluid into the sample path. Moreover, each sample path is operatively switched between the aspiration actuator and the dispensing actuator enabling the micro-metered, non-contact parallel distribution of the reagents or sample fluid to the test site.

Figure 3:
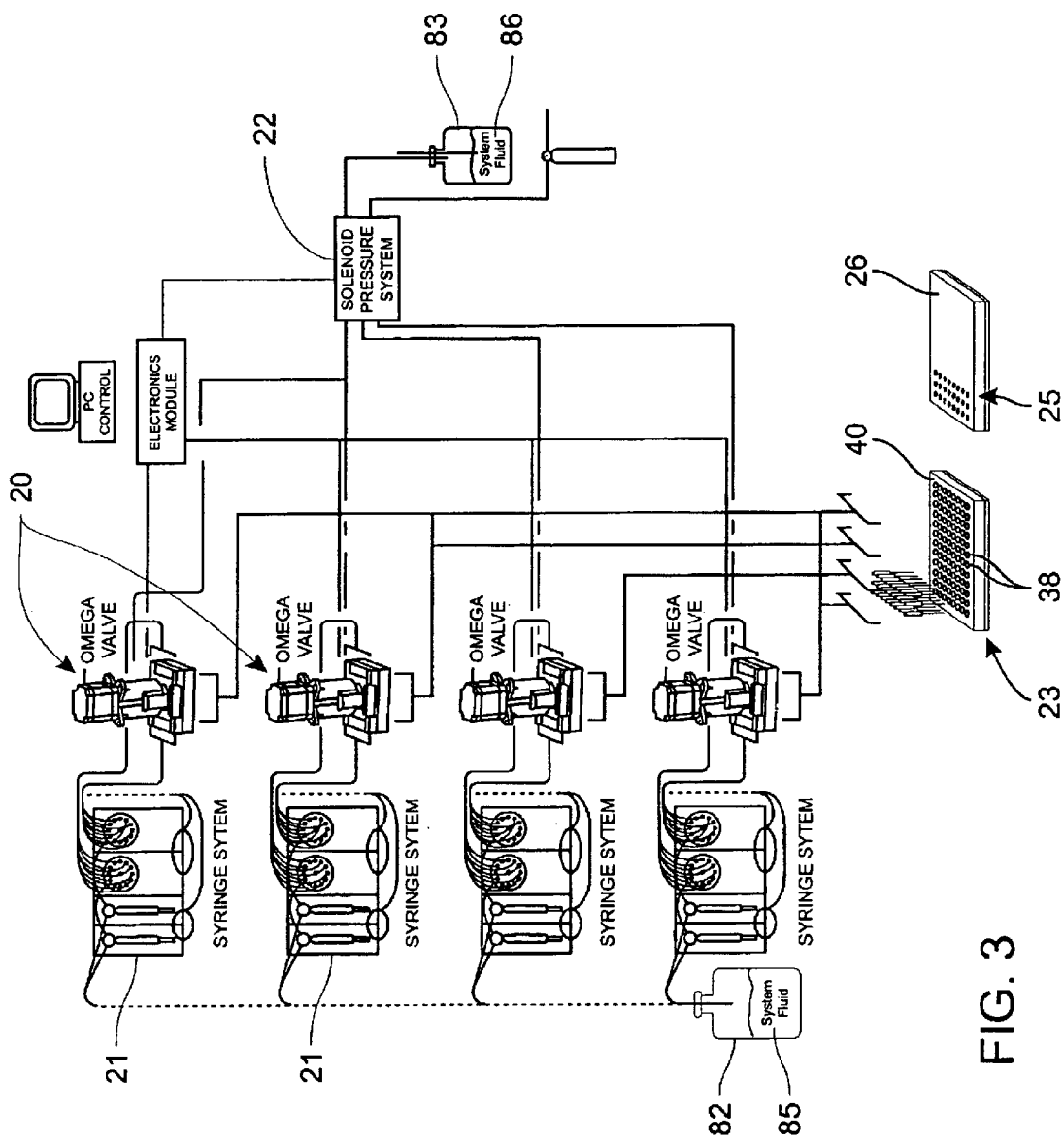
FIG. 3 is a schematic illustration of an assembly incorporating the hybrid valve apparatus of FIG. 1.

As best viewed in the schematic representation of FIG. 3, the present invention is particularly suitable for transferring chemical or biochemical samples or reagents from an array of reservoir wells 38 of a conventional microtiter plate 40, i.e. 96 or 384 wells, to an array of higher-density test sites 25, i.e. a 1536-well microtiter plate, or for fabrication of a chip-based biological sensor (commonly referred to as a "microarray") used for performing gene expression or other screening experiments. Briefly, the hybrid valve apparatus is adaptable for printing arrays wherein the distance between adjacent test sites 25, or test site pitch, is in the range of about 1 micron ($\mu$m) to about 10,000 microns ($\mu$m).

Thus, in the preferred embodiment, the manifold device 28 includes a plurality of fluid aspiration conduits 30, corresponding fluid dispensing conduits 35 and corresponding sample paths 33, which cooperate for the parallel transfer of fluid from the fluid reservoir 23 to the corresponding test sites 25 (FIGS. 3, 4, 13 and 14). Briefly, each fluid aspiration conduit 30 includes a first aspiration port 31 in fluid communication with a corresponding aspiration source or actuator, and an opposite second aspiration port 32 terminating at a stator face surface 41 of the manifold device 28. Moreover, each fluid dispensing conduit 35 includes a first dispensing port 36 in fluid communication with a corresponding dispensing actuator 22, and an opposite second dispensing port 37 also terminating at the manifold stator face 41 as well.

When oriented in the aspiration condition (FIGS. 5, 9 and 10), the valve actuator assembly 27 permits selective fluid communication of the sample paths 33 with the corresponding second aspiration ports 32 of the aspiration conduits 30 at the stator face 41, while simultaneously preventing fluid communication with the corresponding second dispensing ports 37 of the dispensing conduits 35. Conversely, when the valve assembly is oriented in the dispensing condition (FIGS. 6, 11 and 12), the sample paths 33 are moved into selective fluid communication with the corresponding second dispensing ports 37 at the stator face, while simultaneously being moved out of fluid communication with the second aspiration ports 32.

Preferably, the present invention includes twelve (12) independent aspiration conduits 30, and dispensing conduits 35 communicating with corresponding sample paths 33. Thus, inherently, the hybrid valve apparatus 20 may simultaneously deliver sample or reagent fluid to twelve test sites. Other configurations, containing greater of lesser number of independent conduits are possible. It will be appreciated, however, that the system can be configured for a one-to-one transfer of fluid, i.e., from each reagent reservoir to a designated test site. Such flexibility also lends itself to numerous variations of the preferred use. In particular, the hybrid valve apparatus can be configured for transferring sample or reagent fluids from a given number of reservoirs to a different number of test sites. For instance, the switching technology of the hybrid valve manifold device 28 can be designed such that fluid samples from multiple aspiration reservoirs 23 are dispensed on a single test site. Conversely, this manifolding can be adapted for depositing fluid from a single reservoir 23 to multiple test sites.

Figure 2:
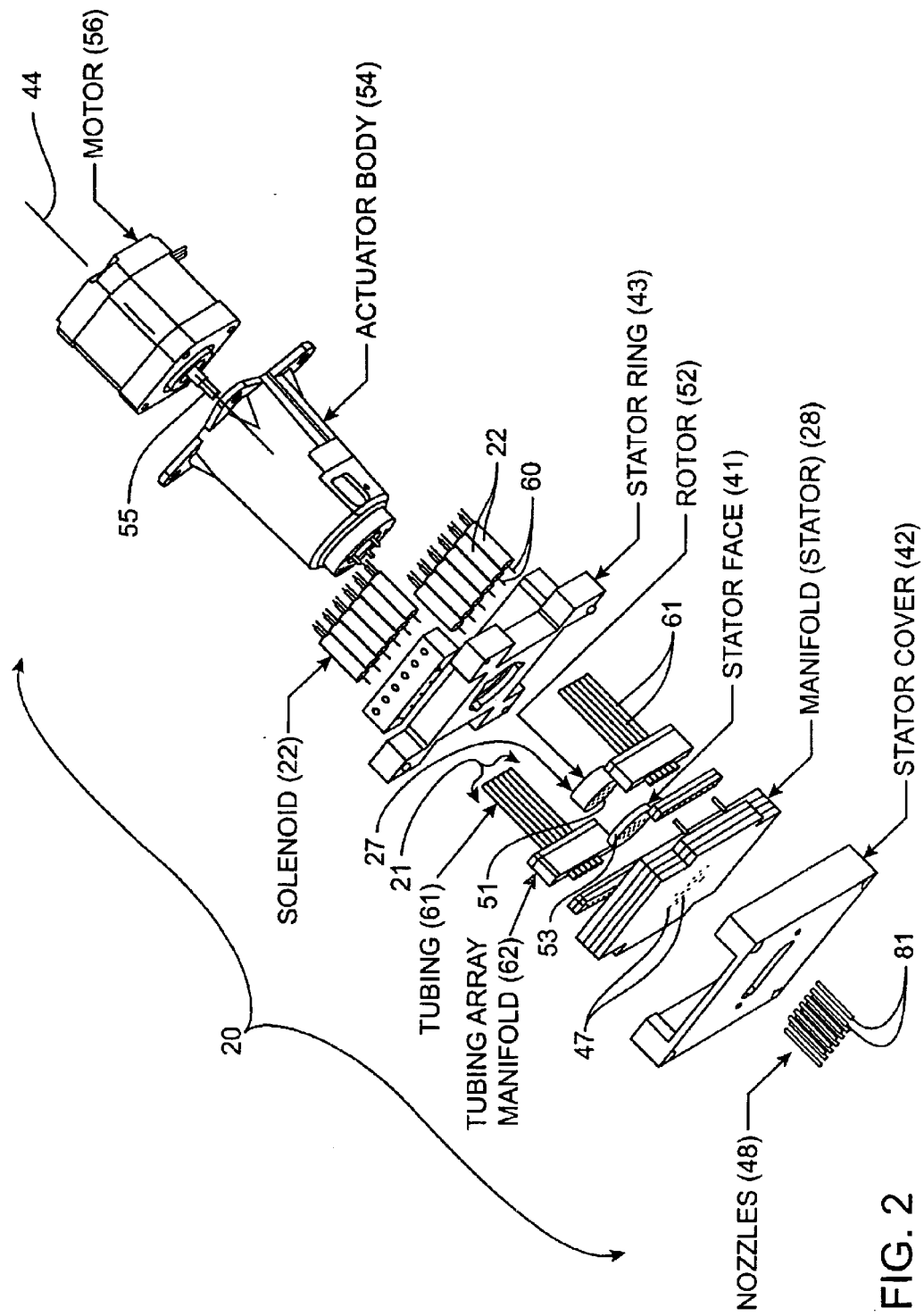
FIG. 2 is an exploded top perspective view of the hybrid valve apparatus of FIG. 1.

Briefly, as shown in FIGS. 1 and 2, the manifold device 28 is preferably sandwiched between a lower stator cover 42 and an upper stator ring 43 for stable support thereof. This assembly cooperates with a track or transport mechanism (not shown) which effects the relative movement between manifold device 28, the fluid reservoirs 23 and the test sites 25 (FIGS. 1 and 3). Preferably, the entire hybrid valve apparatus 20 is transported between the microtiter plates 40 and the array of test sites 25.

Although the hybrid valve apparatus 20 is adapted for simultaneously transferring multiple volumes of fluid sample or reagent to multiple chip test sites, a better understanding of the invention can be gained through a description of the operation thereof with respect to the transfer of the fluids from a single sample path 33 in the manifold device 28. In this description, briefly, the aspiration actuator 21 will be fluidly coupled to the manifold sample path 33, via the valve assembly 27, to aspirate sample fluid from the single reservoir 23 into the sample path. Subsequently, the sample path 33 will be switched, in fluid communication, to the dispensing conduit 35 for finely controlled dispensing of the sample fluid contained in the sample path 33.

Accordingly, FIGS. 5, 6 and 9–12 intentionally depict a single set of fluid transfer elements.

Referring back to FIGS. 5 and 6, in this embodiment, each sample path 33 includes a primary passage portion 45 thereof defined by the manifold device 28. This primary passage portion 45 extends substantially vertically therethrough in a direction substantially parallel to an axis 44 of the hybrid valve apparatus 20. Further, each primary passage 45 includes an upper communication port 46 terminating at the stator face 41, and a lower communication port 47.

Figure 5:
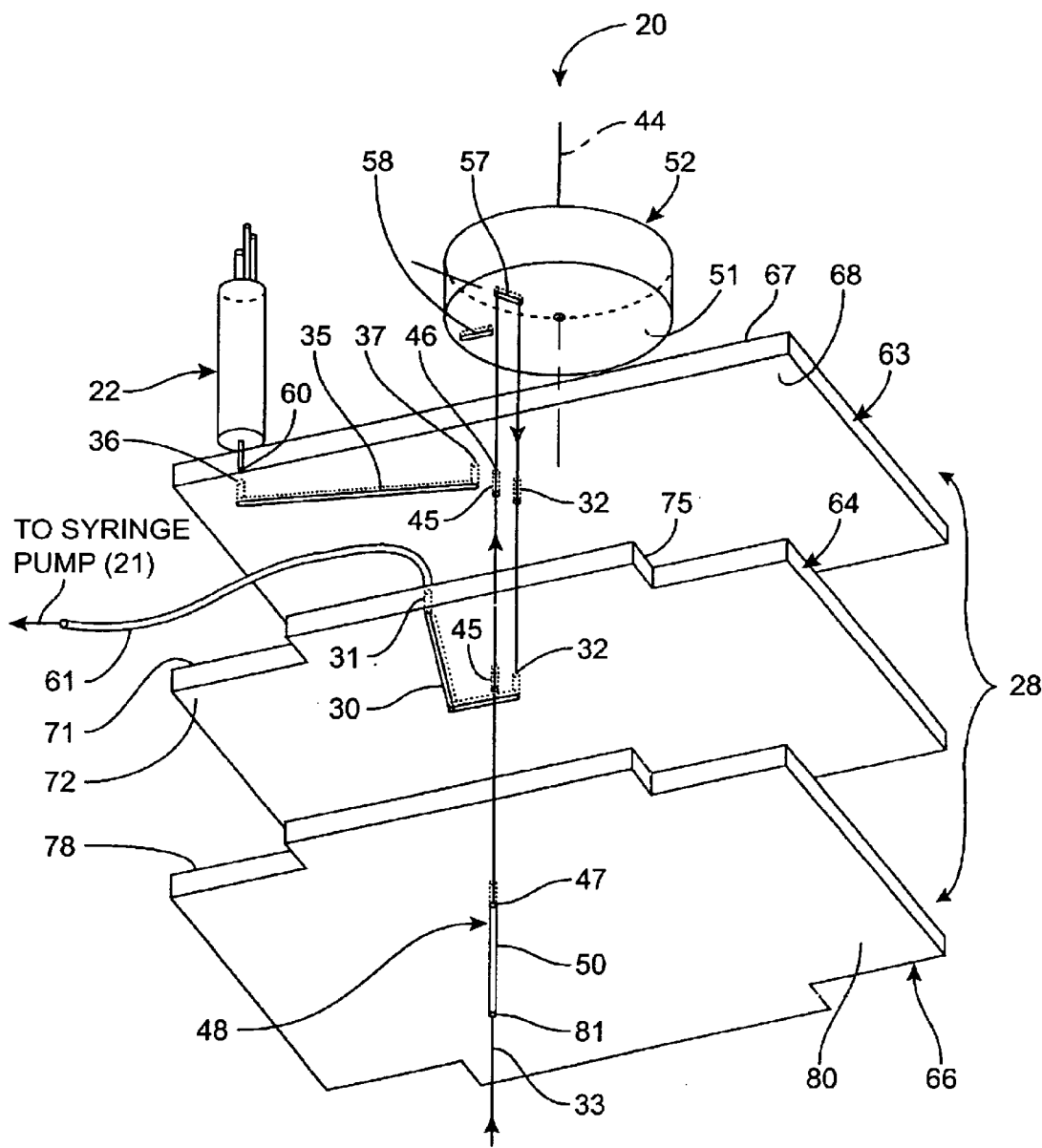
FIG. 5 is an enlarged, exploded bottom perspective view of one fluid path of the hybrid valve apparatus in the aspiration condition.
Figure 6:
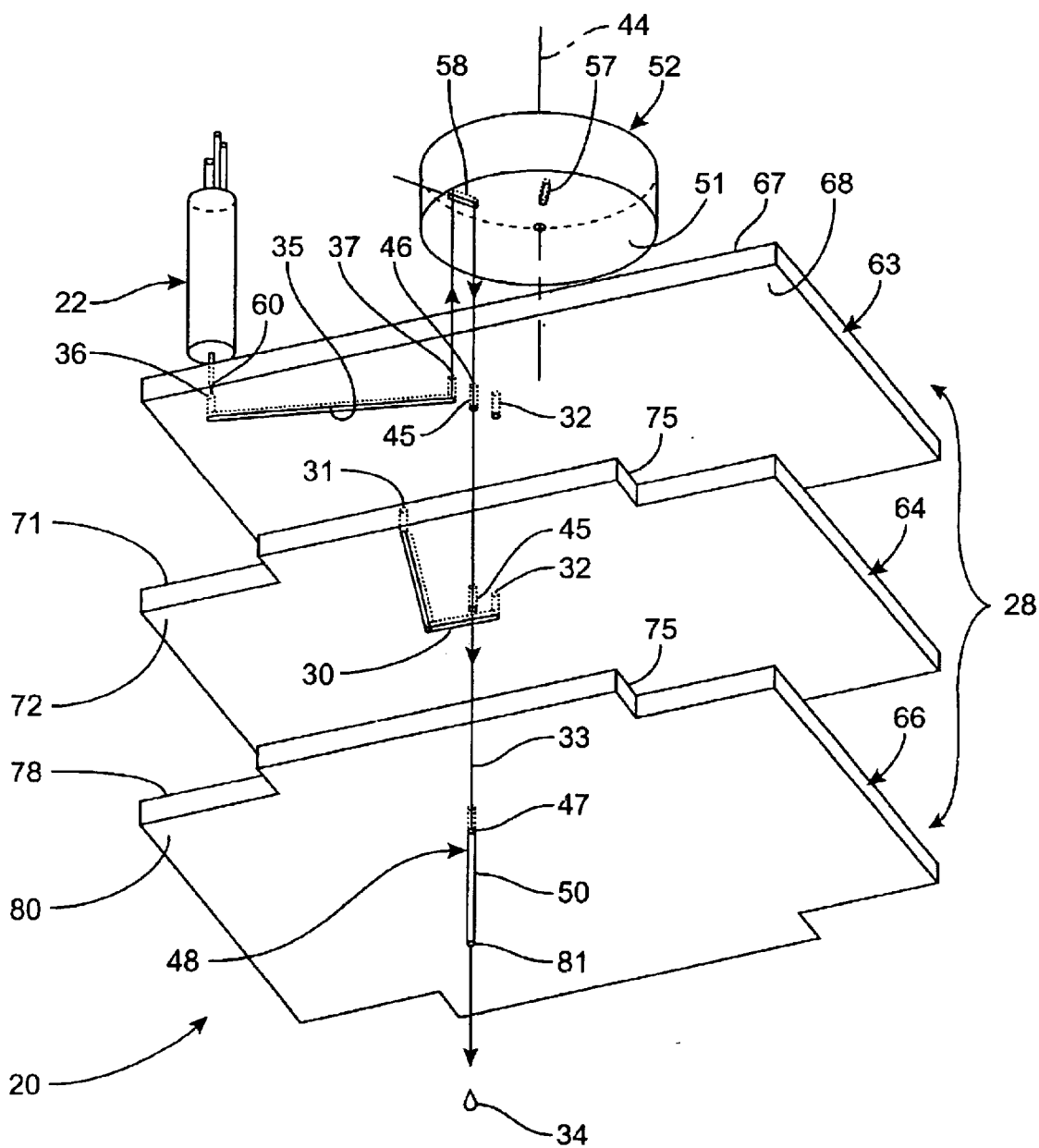
FIG. 6 is an enlarged, exploded bottom perspective view of one fluid path of the hybrid valve apparatus in the dispensing condition.

Preferably, as best illustrated in FIGS. 5 and 6, each primary passage 45 includes a corresponding nozzle member 48 extending outwardly from one of the lower communication ports 47. As will be described in greater detail below, each nozzle member is removably mounted to the manifold device 28 which enables individual aspiration of the sample fluid therein (in the aspiration condition) or individual dispensing of the sample fluid therefrom (in the dispensing condition). Moreover, a nozzle passage 50 extends longitudinally through the nozzle member 48 which inherently increases the volumetric capacity of the corresponding sample path 33.

Figure 8:
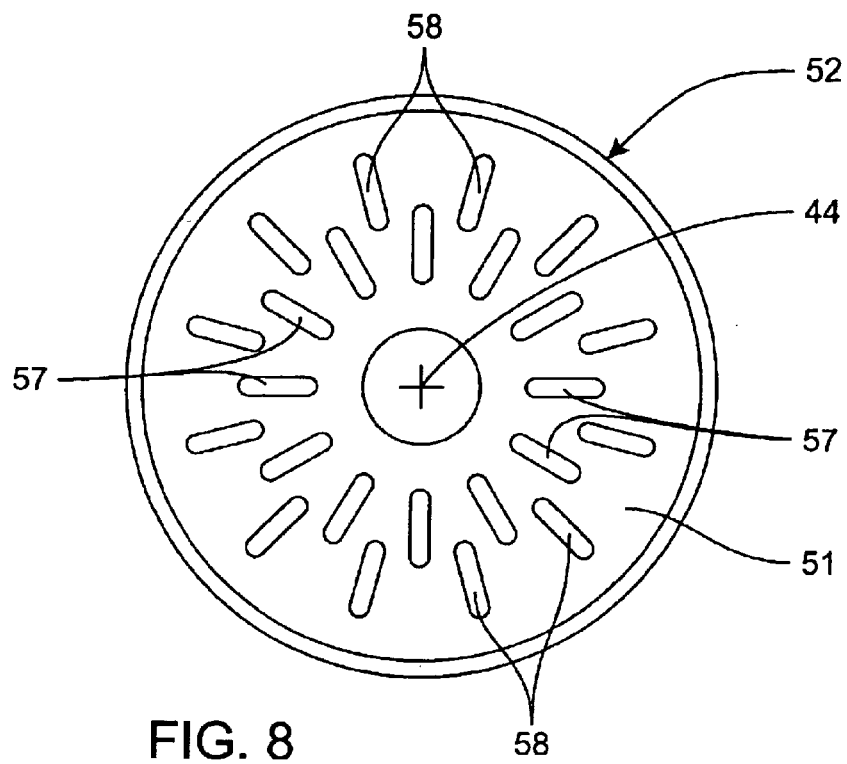
FIG. 8 is an enlarged, bottom plan view of a rotor face of a rotor element of the valve assembly.
Figure 7:
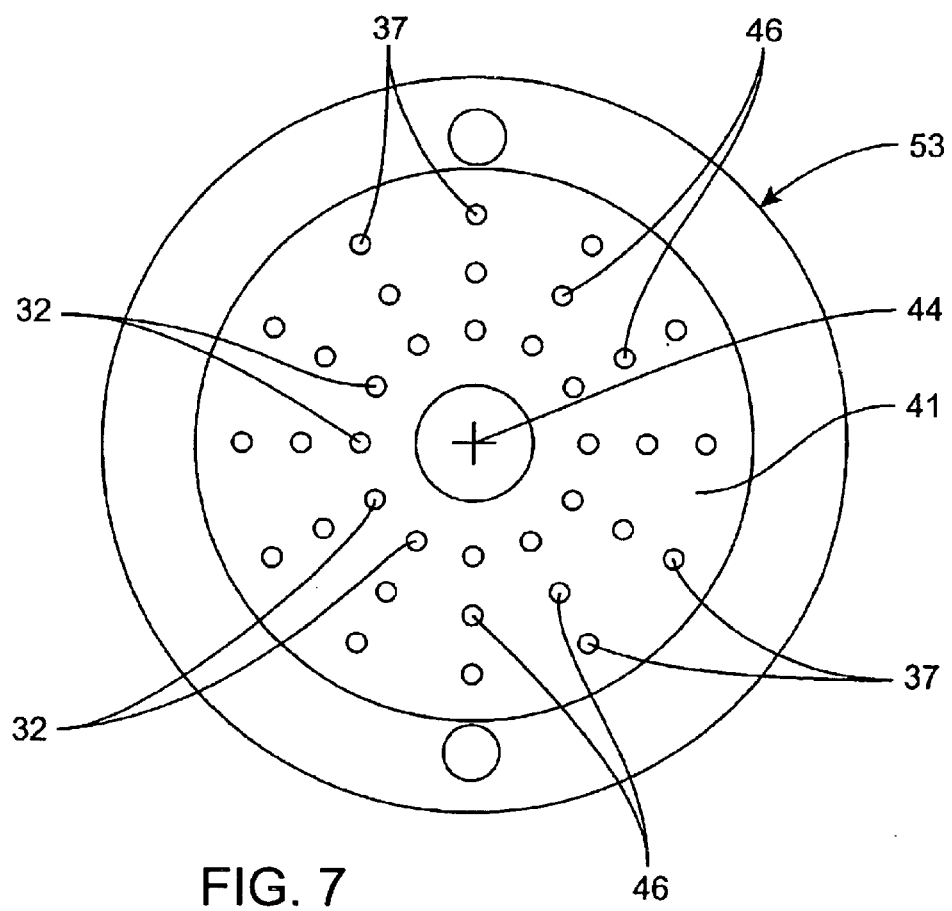
FIG. 7 is an enlarged, top plan view of a stator face of a stator element of the manifold device.

In accordance with the present invention, each of the aspiration conduits 30, the dispensing conduits 35 and the primary passages 45 include a respective port 32, 37 and 46 which terminates at the stator face 41 (FIG. 7) for fluid communication with a rotor face 51 of a rotor element 52 of the valve assembly (FIG. 8). In the preferred embodiment, each of the upper communication ports 46 of the primary passages 45 are equidistant from one another and are radially spaced about a rotational axis of the rotor element 52. Similarly, each of the second aspiration ports 32 and each of the second dispensing ports 37 is also equidistant from one another and radially spaced about the rotational axis 44. FIG. 7 best illustrates, however, that each of the second aspiration ports 32, which incidentally permit fluid communication with the corresponding aspiration actuator 21, are positioned at a radius from the rotation axis 44 smaller than that of the upper communication ports 46, while each of the second dispensing ports 37 are positioned at a radius larger than that of the upper communication ports. Finally, the upper communication ports 46, their corresponding second aspiration ports 32 and dispensing ports 37 are preferably collinearly aligned with a radial line intersecting the rotational axis 44.

It will be appreciated, however, that the corresponding ports can be alternatively spaced and oriented without departing from the true spirit and nature of the present invention. For example, while the collinear alignment between the corresponding ports 32, 37 and 46 is preferred, it is not a requirement for functionality of the manifold device, as will be apparent.

Further, whether the second dispensing ports 37 and the second aspiration ports 32 are at a radial distance less than or greater than the radial distance of the upper communication ports 46 of the primary passages 45 from the rotational axis 44 is not determinative.

In accordance with the present invention, the valve assembly 27 and manifold device 28 are particularly suitable to the application of shear valve or flat face valve technology even though a rotary plug, a bank of 3-way solenoid valves, or MEMS device could be used. Thus, turning now to FIGS. 2, 5, 6 and 8, the valve assembly 27 is illustrated having rotor element 52 which provides the contact or rotor face 51 in opposed sliding contact with the stator face 41 at a rotor-stator interface. This high pressure sliding contact between the stator face 41 and the rotor face 51 provide a selective switching function between each of the sample paths 33 (i.e., the primary passage 45 and nozzle passage 50) and the corresponding aspiration actuators 21 or dispensing actuators 22, depending upon whether the rotor element 52 of the valve assembly 27 is in the aspiration condition or the dispensing condition.

Briefly, both the rotor element 52 and the stator face element 53 are composed of conventional shear valve or flat face valve materials which are adapted to support the high pressure contact at the stator-rotor interface. Typical of these materials include ceramic and synthetic composition, many of which are proprietary in nature. The rotor element 52 is rotatably mounted to a shaft which in turn is connected to a gear reduction inside the actuator body 54. The gear reduction is then coupled to the motor shaft 55 of a conventional electric motor 56 applied in shear valve or flat face valve technology.

As best shown in FIG. 8, the rotor element 52 of the valve assembly 27 provides a plurality of spaced-apart aspiration channels 57 and dispensing channels 58 which are slotted in the substantially planar rotor face 51 thereof. Each aspiration channel 57 and each dispensing channel 58 is elongated in shape, and extends generally along a radial line intersecting the rotational axis 44 of the rotor face 51. Further, the aspiration channels 57 and the dispensing channels 58 are equally spaced and are oriented in an alternating manner, relative one another. Accordingly, at the rotor-stator interface (i.e., the high pressure sliding contact between the stator face 41 and the rotor face 51), the rotor element 52 either reciprocates or rotates in one direction clockwise or counter clockwise to orient the valve assembly in the aspiration condition or the dispensing condition.

Figure 9:
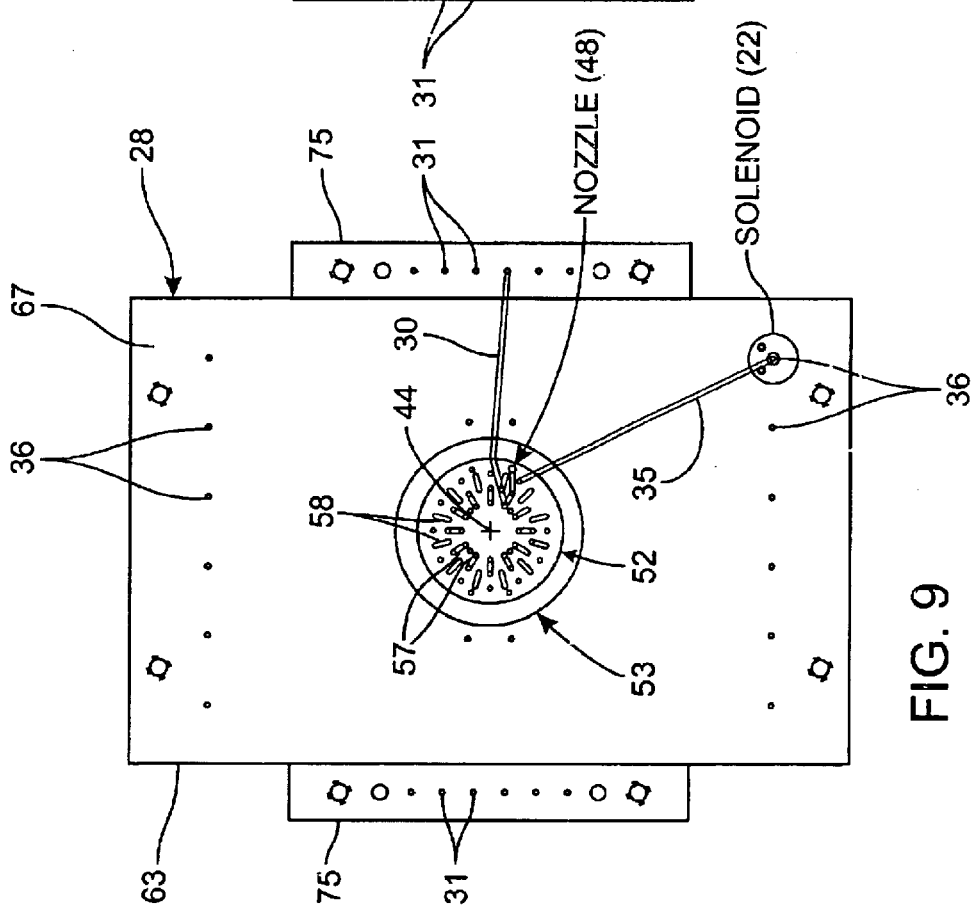
FIG. 9 is a top plan view of the manifold device with the rotor face superimposed over the stator face at a rotor/stator interface in the aspiration condition.

When the rotor element 52 rotates about the rotational axis 44 to the aspiration condition, the aspiration channels 57 slotted into the rotor face 51 are rotated into alignment with the corresponding upper communication port 46 of the primary passages 45 and the second aspiration ports 32 of the aspiration conduits 30 of the stator face 41 to provide a fluid communication path therebetween (FIGS. 5, 9 and 10). Consequently, a fluid path is created by the aspiration channel 57 between the corresponding sample path 33 and the corresponding aspiration actuator 21. This permits selective aspiration of the fluid sample or reagent, via the aspiration actuator 21, from the sample reservoir 23 into the sample path 33 through the nozzle member. Simultaneously, in the aspiration condition, the second dispensing ports 37 of the dispensing conduits 35 are dead-ended into the rotor face 51 of the rotor element 52. Thus, the dispensing actuators 22 are out of fluid communication with the corresponding sample paths 33.

Figure 11:
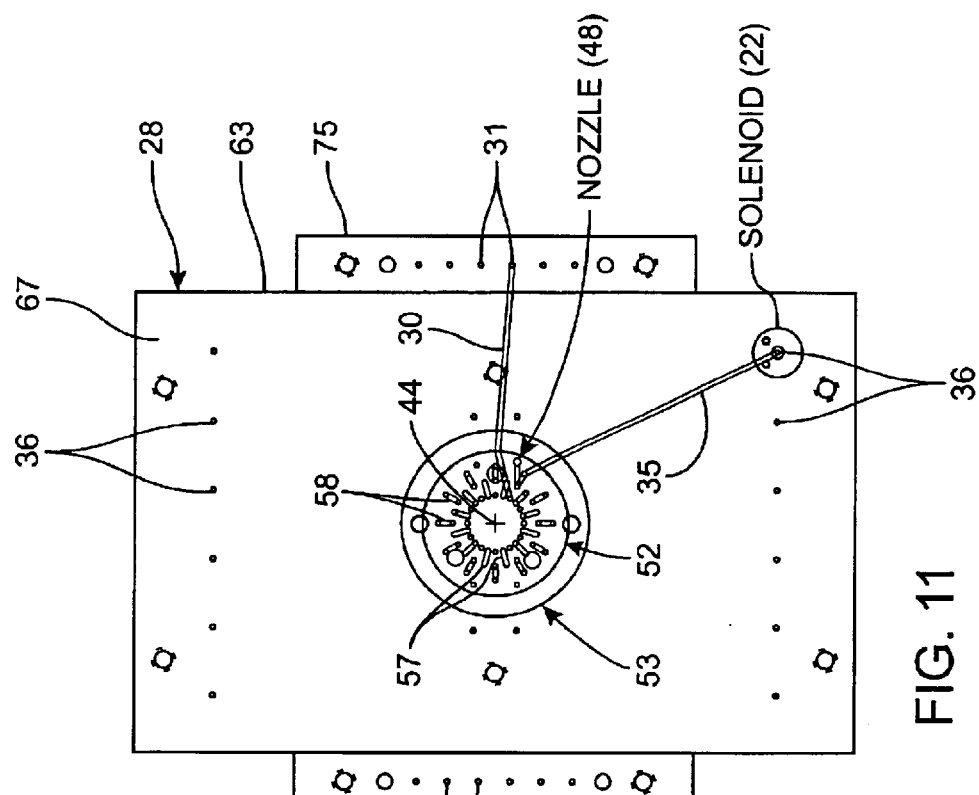
FIG. 11 is a top plan view of the manifold device of FIG. 9 in the dispensing condition.

Subsequently, as FIGS. 6, 11 and 12 illustrates, the rotor element 52 can be selectively rotated about rotational axis 44 to the dispensing condition. The radially extending dispensing channels 58, also slotted into the rotor face 51, are consequently rotated into collinear alignment with the corresponding upper communication ports 46 and the second dispensing ports 37 of the dispensing conduits 35 to provide a fluid communication path therebetween. The dispensing channels 58, thus, complete the fluid path between the corresponding sample path 33 and the corresponding dispensing actuator 22 to permit selective dispensing, via the dispensing actuator 22, of the fluid sample or reagent contained in the respective sample path 33. Similarly, in the dispensing condition, the second aspiration ports 32 of the dispensing conduits 35 are dead-ended into the rotor face 51 of the rotor element 52. Thus, the aspiration actuators 21 are out of fluid communication with their corresponding sample paths 33. Further, it will be appreciated that all twelve, or any number of, sample paths 33 can be simultaneously aspirated or dispensed.

Accordingly, the shear valve and manifold device arrangement of the present invention provides an accurate switching functionality between the aspiration actuators and the dispensing actuators. As above-indicated, such switching capability is beneficial in that the full potential of the high speed, precision ink-jet style dispensing actuators can be exploited to dispense the sample fluids or reagents from the sample paths. Moreover, the modular parallelism of system facilitates fabrication of non-contact devices, e.g. 24, 48, 96-tip, suitable to the expanding needs of the market.

It will be understood that while the valving functionality of the present invention is particularly adaptable for flat face or shear valves, other valve technologies are suitable such as solenoid valves, pinch valves and micromachined valves, actuated by mechanical, electrical or pneumatic means.

Moreover, each dispensing conduit 35 includes an independent dispensing source 22 fluidly coupled to its corresponding first dispensing port 36 thereof. As best illustrated in FIGS. 1 and 2, the dispensing actuators 22 are preferably mounted to a corresponding dispensing actuator manifold device 28. These two opposed dispensing actuator manifolds separate and align the individual dispensing actuators into two sets of six actuators releasably mounted to the stator manifold device 28 as a unit. Each dispensing actuator 22 includes a delivery orifice 60 which is fluidly coupled to a corresponding first dispensing port 36 of the dispensing conduit 35.

In the preferred embodiment, each dispensing actuator 22 typically delivers a metered pressure pulse using a pressure ranging from about $6.9(10)^3$ N/m$^2$ to about $138(10)^3$ N/m$^2$, and having a duration ranging from about $(10)^{-6}$ seconds to about 10 seconds. Preferably, the dispensing actuator 22 is provided by a conventional ink-jet style printing valve or pump designed for drop-on-demand printing. Ink-jet style printing valves/pumps for drop-on-demand printing, including thermal, solenoid and piezoelectric types, are commercially available and well known in the art. For instance, the Lee Company of Essex, Connecticut manufactures a solenoid-based ink-jet valve (Model No. INKX0502600AB) which is suitable for use with the present invention. Alternatively, conventional syringe pumps may be employed for metering as well.

The incorporation of ink-jet drop-on-demand printing technology into the dispense assembly of the present invention provides significant advantages vis-a-vis known systems for printing microarrays. In particular, the ability to deliver independent, short-duration, pressure pulses associated with ink-jet print valves enables the non-contact tunable delivery of reagent sample volumes in the range of about $(10)^{10}$ to about $(10)^{-12}$ liters. Upon application of a pressure pulse, at least one droplet of sample or reagent fluid is ejected from the manifold sample path through the corresponding nozzle member 48 onto substrate surface 26. As used herein, the term "non-contact" refers to the lack of contact between the dispense manifold and nozzles, and the target substrate during deposition. Typically, in these designs, the fluid is communicated through channels micromachined into an ink-jet style printhead—such as those commonly used in desktop and industrial printers.

Preferably, these ink-jet drop-on-demand dispensing actuators are coupled to digitally regulated hydraulic pressure systems (not shown). These systems enable precise manipulation of hydraulic pressure supplied to the dispensing actuators expanding the dynamic range of the system. An added benefit is the ability to quickly change the pressure range to compensate for differences in samples due to particulates or viscosity.

The aspiration source 21, on the other hand, are preferably provided by individual aspiration actuators 21 fluidly coupled to a corresponding first aspiration port 31 through tubing 61. These tubes 61, which are preferably inert plastic or the like having an inner diameter in the range of 0.2 mm to about 3.0 mm, are also separated into two banks of six units and each have a distal end coupled to a tubing array manifold 62. In turn, these opposed tubing array manifolds 62 are mounted to the stator manifold device 28 as a unit.

It will be appreciated that more than one or all of the aspiration conduits 30 can be fluidly coupled to a single aspiration actuator 21. In the preferred form, the aspiration actuator 21 is provided by an external metering device such as a syringe-type pump or a diaphragm pump, or by a pressurized source delivering a positive or negative pressure to the aspiration conduits 30. Typical of these aspiration devices is Model # 2009D provided by Innovadyne Technologies, Inc., Rohnert Park, Calif.

In another aspect of the present invention, the manifold device 28 is comprised of a plurality of stacked plate members 63–66 which collectively cooperate to channel the sample fluids from the reservoir wells to the designated test sites 25, via the valve assembly 27. As above-indicated, the manifold device 28 defines a plurality of primary passages 45, aspiration conduits 30 and dispensing conduits 35 each of which includes a communication port terminating at the stator face for communication with the valve assembly 27.

Since these individual conduits are independent of one another, fabrication is difficult for such a small scale. Typically, the diameter of these fluid passages is on the order of about 0.001 mm to about 1.0 mm. Moreover, these conduits and passages must be capable of accommodating the relatively high pressure pulses of the dispensing actuators 22 which as mentioned have a range from about $6.9(10)^3$ N/m$^2$ to about $138(10)^3$ N/m$^2$, and have a duration in the range from about $(10)^{-6}$ seconds to about $(10)^1$ seconds.

The plate members 63–66 (FIGS. 4 and 13) are preferably rectangular in shape, each having a substantially planar topside and an opposed bottom side. More particularly, the manifold device 28 includes a first plate member 63 having a topside surface 67 upon which the disk-shaped stator face element 53, defining the stator face 41, is supported. On an opposite side of the topside surface 67 of the first plate member 63 is a bottomside surface 68 upon which a plurality of horizontally extending dispensing grooves 70 are formed. These grooves are preferably about 0.3 mm in width and are about 1.0 mm deep into the bottomside surface 68, depending upon the particular application. A corresponding first dispensing port 36 extends vertically into the first plate member 63 from the topside surface 67 to the bottomside surface 68 where it intersects one end of a corresponding dispensing groove 70. Similarly, a corresponding second dispensing port 37 extends vertically into the stator face element 53 and first plate member 63 from the stator face 41 to the bottomside surface 68 where it intersects an opposite end of a corresponding dispensing groove 70.

In accordance with this aspect of the present invention, a substantially planar topside surface 71 of the second plate member 64 is affixedly lamination or diffusion bonded to the bottomside surface 68 of the first plate member 63 at a first plate/second plate interface. Hence, the diffusion bonded second plate member topside surface 71 effectively seals the dispensing grooves 70 extending into the bottomside surface 68 of the first plate member 63 to form the corresponding dispensing conduits 35.

It will be appreciated that the groove formation forming the horizontal portions of the dispensing conduits 35 could be provided by both the bottomside surface 68 of the first plate member 63 and the topside surface 71 of the second plate member 64, or alternatively, only by the second plate topside surface. It will further be understood that the alignment and orientation of first dispensing ports 36 can be positioned at a plurality of locations along the topside surface of the first plate member without departing from the true spirit and nature of the present invention.

Applying a similar technique, the aspiration conduits 30 could also have been defined at the first plate/second plate interface. However, to assure sufficient spacing between adjacent conduits to accommodate high pressure nature of the fluid delivery, the aspiration conduits 30 are preferably formed at a separate second plate/third plate interface between the second plate member 64 and a third plate member 65. Thus, the bottomside surface 72 of the second plate member preferably incorporates a plurality of horizontally extending aspiration grooves 73 (FIGS. 13 and 14) which are preferably about 0.5 mm in width and are about 0.25 mm deep.

A corresponding first aspiration port 31 extends vertically into the second plate member 64 from the topside surface 71 to the bottomside surface 72 thereof where it intersects one end of a corresponding aspiration grooves 73. It will be appreciated that the second plate member includes a pair of opposed wing portions 75 which extend beyond the peripheral edge of the first plate member 63. Briefly, these wing portions 75 are adapted to accommodate the mounting of the tubing array manifolds 62 thereto. Regarding the second dispensing ports 37, however, these aligned vertical passages extend from the stator face 41 of the stator face element 53 through both the first plate member 63 and the second plate member 64 to the bottomside surface 72 thereof where it intersects an opposite end of a corresponding aspiration groove 73.

Similar to the formation of the dispensing conduits 35, a substantially planar topside surface 76 of the third plate member 65 is affixedly coupled to the bottomside surface 72 of the second plate member 64 at the second plate/third plate interface. Again, applying conventional lamination or diffusion bonding techniques, the third plate topside surface 76 can be laminated to the second plate bottomside surface 72 to effectively seal the aspiration grooves 73 to form the corresponding aspiration conduits 30.

Figure 4B:
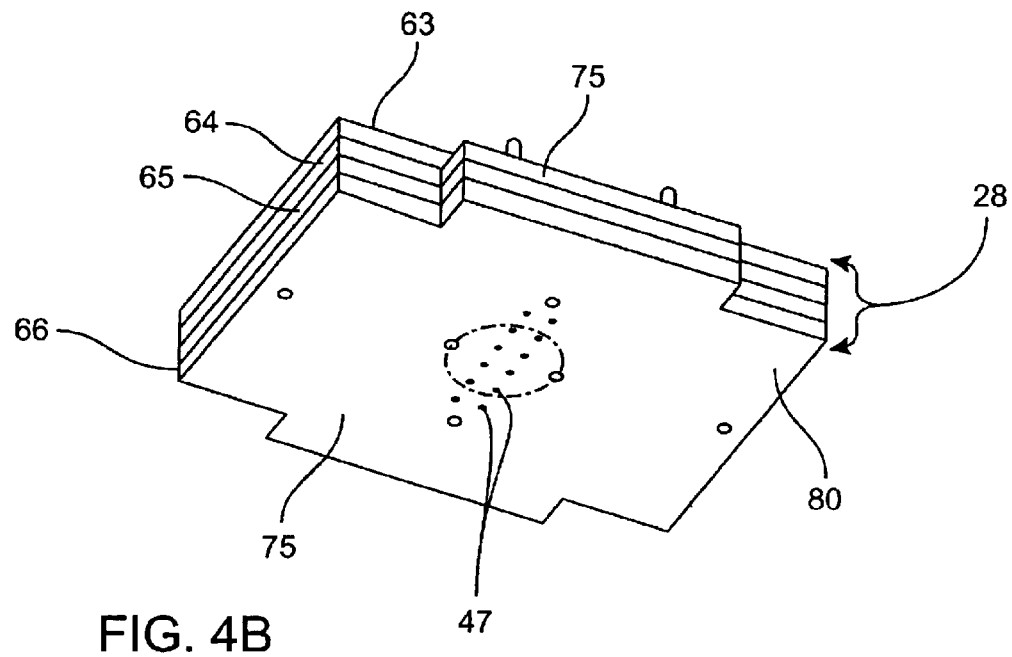
FIG. 4B is a bottom perspective view illustrating the lower communication ports of the manifold device of FIG. 4A.
Figure 4A:
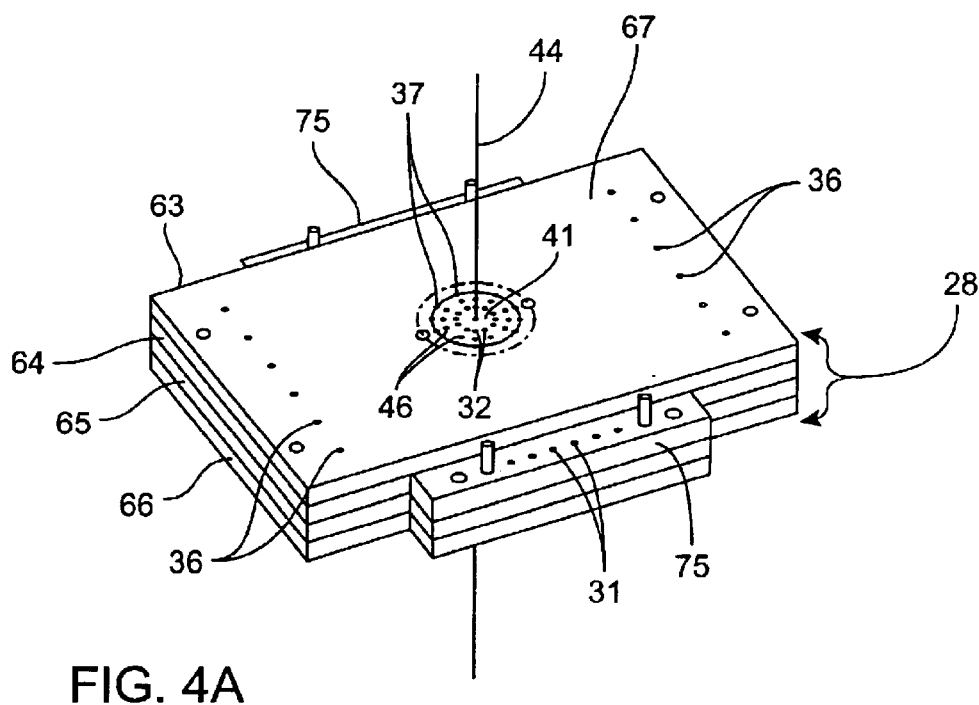
FIG. 4A is a top perspective view of a manifold device of the hybrid valve apparatus of FIG. 1, and illustrating the stator face interface.
Figure 13:
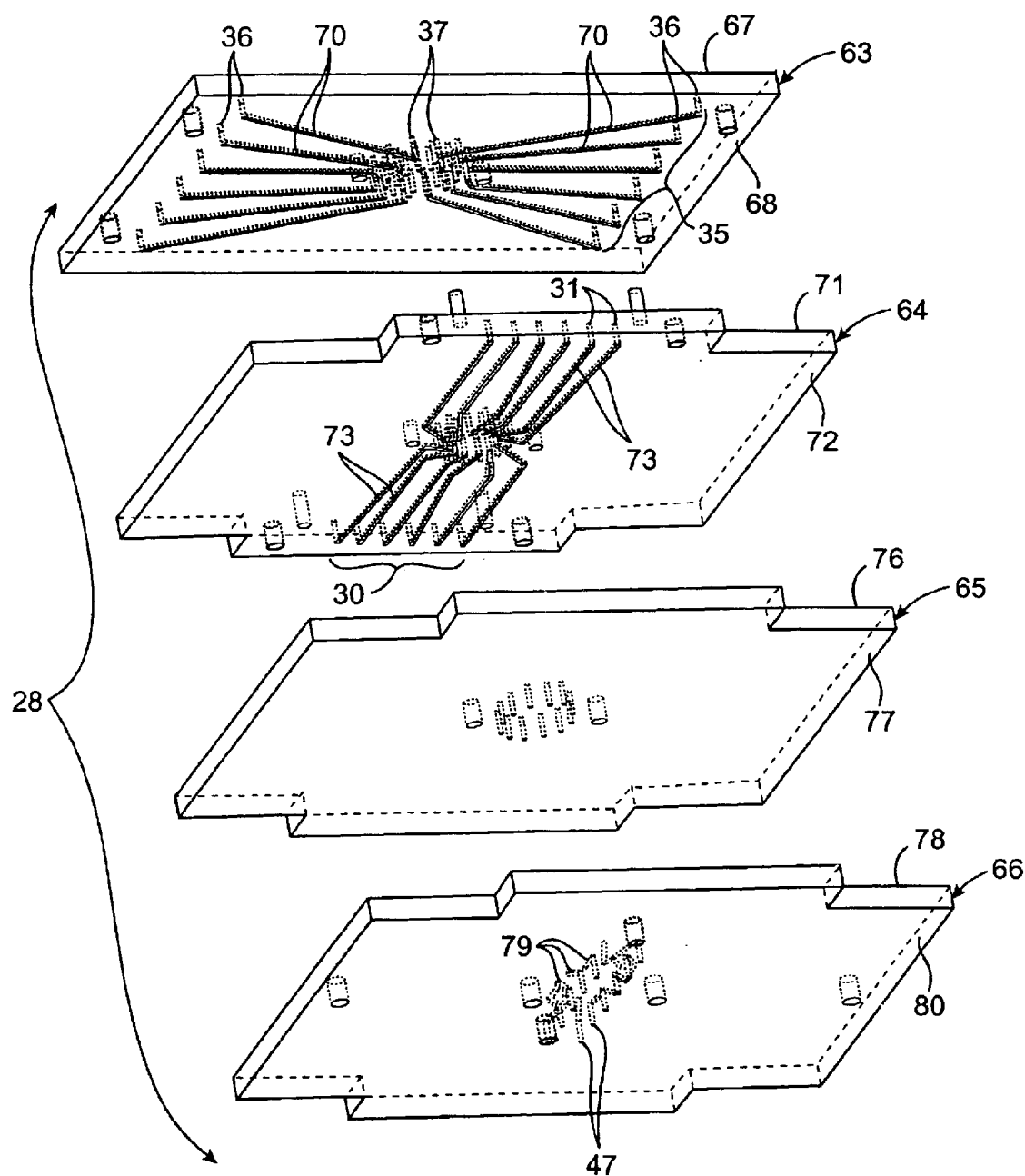
FIG. 13 is an exploded, enlarged bottom plan view of the manifold device of FIG. 4B, illustrating the channels and grooves of the individual plate members.
Figure 14:
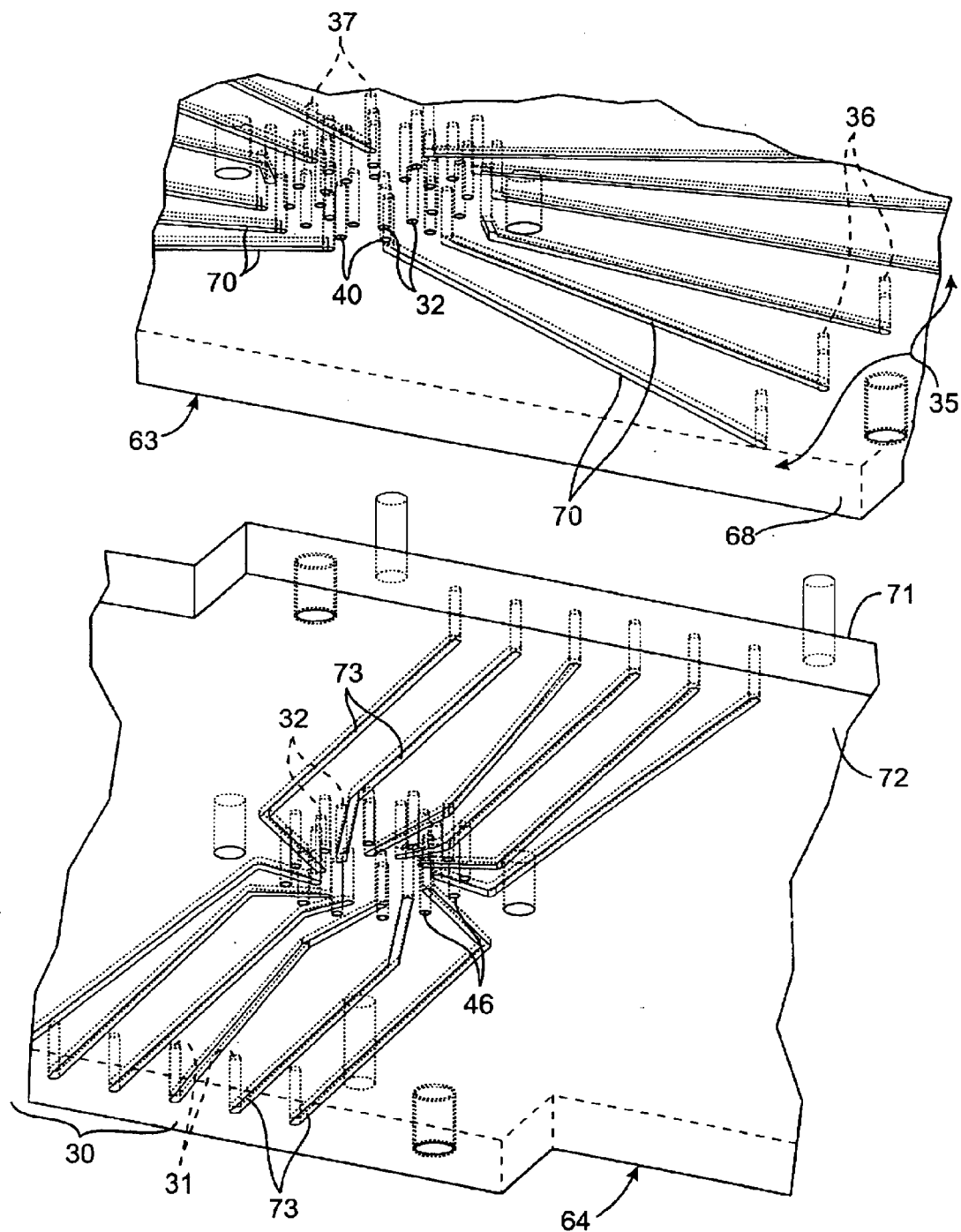
FIG. 14 is an enlarged, fragmentary, illustration of the exploded bottom plan view of FIG. 13.

As best viewed in FIGS. 4A and 13, the circular pattern of the upper communication port 46 extend vertically through the stator element 53. The first plate member 63, the second plate member 64 and the third plate member 65 also include corresponding co-axially aligned passage components to collectively form the primary passages 45 of the sample paths 33 when the manifold plate members are laminated together. Typically, the transverse cross-sectional area of primary passages 45 are on the order of about 0.2 mm$^2$ to about 0.8 mm$^2$ from the stator face 41 to a bottomside surface 77 of the third plate member 65.

To reorient the circular pattern of the upper communication port 46 at the bottomside surface 77 of the third plate member 65 to a rectangular pattern of the lower communications ports 47, which conforms to the spacing of the array of reservoir wells 38 of the microtiter plate 40 and test sites 25, a fourth plate member 66 is required. As shown in FIGS. 10, 12 and 13, a fourth topside surface 76 of the fourth plate includes a plurality of horizontally extending repositioning grooves 79. These grooves 79 are preferably about 0.5 mm in width and are about 0.25 mm deep into the topside surface 76 of the fourth plate member 66. A corresponding lower communication port 47 extends vertically into the fourth plate member 66 from a bottomside surface 80 to the topside surface 78 thereof where it intersects one end of a corresponding repositioning groove 79. The other end of the repositioning groove 79 is aligned with the corresponding primary passage 45 terminating at the bottomside surface 77 of the third plate member 65. Again, applying conventional lamination or diffusion bonding techniques, the fourth plate topside surface 78 can be diffusion bonded to the third plate bottomside surface 77 to effectively seal the repositioning grooves 79 to form another portion of the sample path 33.

As above-mentioned and as illustrated in FIGS. 2, 5 and 6, fluidly coupled to each lower communication port 47 of the primary passage 45 is a corresponding nozzle member 48 having a nozzle passage 50 extending therethrough. The elongated nozzle member 48 includes a distal tip portion 81 suitably dimensioned to extend into a targeted reservoir well 38, in aspiration condition, to aspirate sample or reagent fluid into the sample path 33. Moreover, the 2×6 array of nozzles are spaced apart to conform with the array of reservoir wells and test sites 25 for simultaneous aspiration and dispensing. They can also be redistributed to other formats such as 1×12.

In the preferred embodiment, the diameter of the nozzle 50 passages abruptly changes to a smaller diameter by means of an orifice, such as a jeweled orifice. This change in diameter is beneficial in that it facilitates ejection of the sample fluids from the tip when a pressure pulse is delivered by the corresponding dispensing actuator 22.

As shown in FIG. 3, system fluid reservoirs 82, 83, containing conventional mobile phase fluid 85, 86, are supplied to the aspiration actuators 21 and the dispensing actuators 22 as a driving fluid. In the aspiration condition, when rotor element 52 of the valve assembly 27 is rotated to align the corresponding aspiration channels 57 to the corresponding upper communication ports 46 of the primary passages 45 of the sample paths 33 and the second dispensing ports 37 of the aspiration conduits 30, the aspiration actuators 21 can be first employed to purge the entire path from the first aspiration port 31 of the aspiration conduit all the way to the corresponding dispensing orifice of the tip 81 of the nozzle member 48. Thus, after the nozzle tips are optionally cleaned, clean mobile phase fluid replaces any sample or reagent fluid from previous operations.

The transport mechanism (not shown) is then operated to position the hybrid valve assembly 27 at the reservoir wells 38 where the designated nozzle tips 81 are submersed in the targeted reservoir wells. Operation of one or more of the syringe pumps 21 draw the sample or reagent fluids into the corresponding sample path 33 in the manifold device 28. The volume of fluid aspirated into the corresponding sample path 33, thus, can be accurately metered.

Subsequently, the transport mechanism can move the hybrid valve assembly 27 to the test sites 25, while the electric motor 56 and drive train 54 rotates the rotor element 52 from the aspiration condition to the dispensing condition. As mentioned, the aspiration channels 57 in the rotor face 51 are moved out of fluid coupling to the upper communication ports 46 of the primary passages 45, while the dispensing channels 58 in the rotor face 51 are moved to fluidly couple the second dispensing ports 37 of the dispensing conduits 35 with the corresponding communication ports 46. Essentially, in the aspiration condition, the second dispensing port 37 of the dispensing conduit 35 is dead-ended against the rotor face 51, while in the dispensing position, the second aspiration port 32 of the aspiration conduit 30 is dead-ended against the rotor face 51.

The mobile phase fluid, which is preferably substantially similar to that supplied to the aspiration actuators, is fluidly coupled to the corresponding is dispensing channels 58 in the rotor face 51 to selectively dispense the sample fluids from the corresponding nozzle tips 81. Accordingly, cross-contamination is minimized to the mobile phase fluids contained in the corresponding dispensing channels 58. This assures that the dispensing conduits 35 can be substantially maintained free of contamination of any sample or reagent fluids.

In an alternative embodiment of the present invention, the nozzle passages 50 and corresponding primary passages 45 may only be employed to dispense the sample or reagent fluid from the sample path 33. Unlike the embodiment above-mentioned, the nozzle member 48, thus, will not be utilized to aspirate the targeted fluid into the sample path from the source plate. Accordingly, as viewed in the embodiments of FIGS. 15 and 17, the hybrid valve assembly can load the sample path 33 through means other than the nozzle members 48, while maintaining the isolation of the sample path from the dispensing actuator, in the aspiration condition (FIGS. 15 and 17), and isolation of the sample path from the aspiration actuator, in the dispensing condition (FIGS. 16 and 18).

Briefly, the manifold body in this configuration includes a source conduit, generally designated 87, having an upper communication opening 88 terminating at the stator face 41, and an opposite end in fluid communication with the source reservoir 23. Further, as best viewed in FIGS. 15, 17 and 19, the contact or rotor face 51 of the valve body or rotor element 52 includes a sample channel 90 which, in the aspiration condition, fluidly couples the second aspiration port 32 of the aspiration conduit 30 to the upper communication opening 88 of the source conduit 87.

Figure 17:
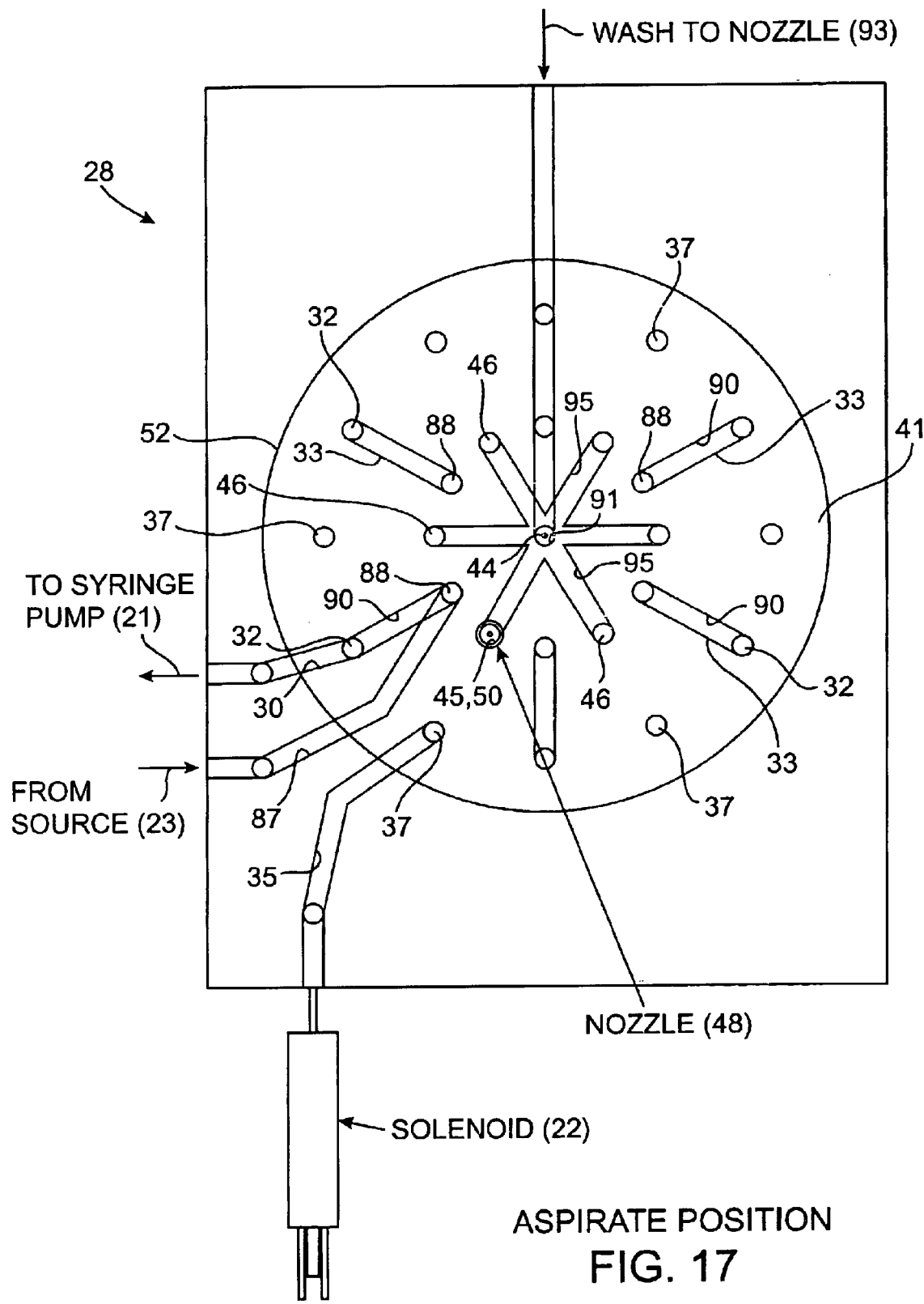
FIG. 17 is an enlarged top plan view of the rotor/stator interface of FIG. 15, in the aspiration condition.

Accordingly, in the aspiration condition, the aspiration actuator 21 is fluidly coupled to the source reservoir through the sample channel 90 formed in the rotor face 51. Upon activation of the aspiration actuator, the reagent or sample fluid can be drawn into the sample path 33 by way of the source conduit 87 in the manifold body 28. To isolate the dispensing actuator 22 from the sample path 33, the corresponding second dispensing port 37 of the dispensing conduit 35 is dead-ended into the rotor face 51, and thereby out of fluid communication with the sample path (FIG. 17).

Figure 16:
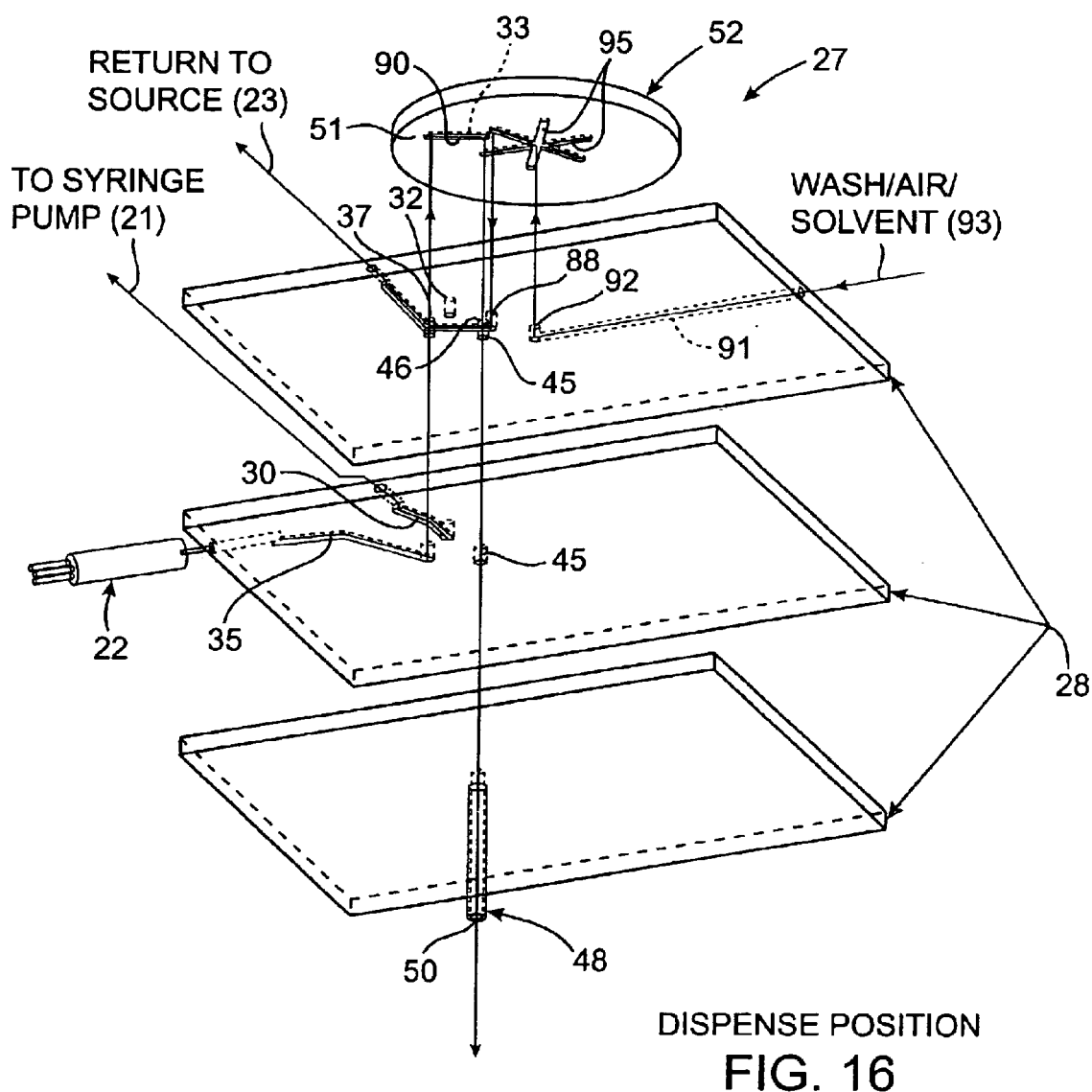
FIG. 16 is an exploded bottom perspective view of one fluid path of the alternative embodiment hybrid valve apparatus of FIG. 15, in the dispensing condition.
Figure 18:
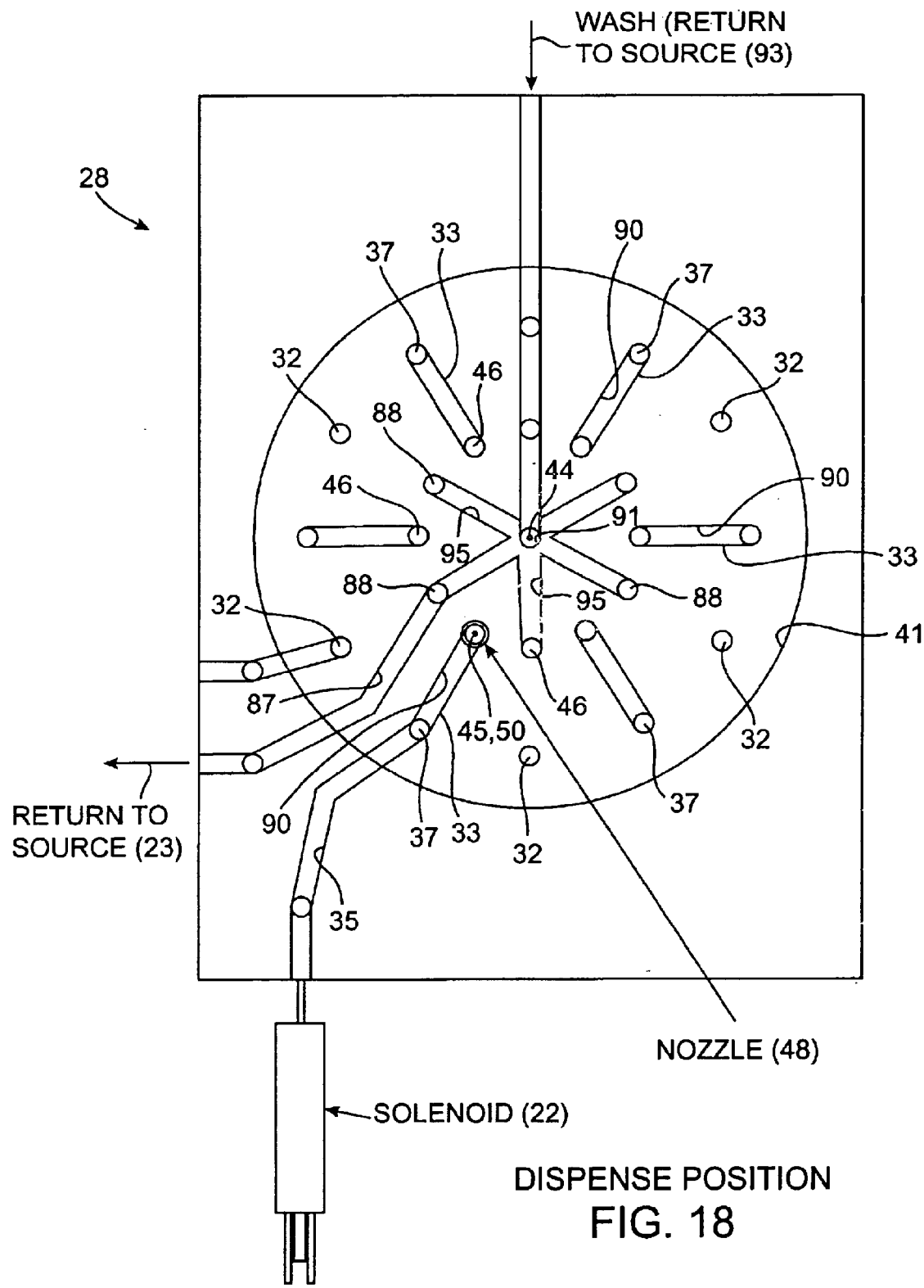
FIG. 18 is an enlarged top plan view of the rotor/stator interface of FIG. 16, in the dispensing condition.

Once the reagent or sample fluid is aspirated into the sample path 33, via the aspiration actuator 21, the valve assembly 27 can be moved to the dispense position of FIGS. 16 and 18. In the preferred form, the rotor element 52 of the valve assembly is rotated about rotational axis 44 for movement from the aspiration condition to the dispense condition. The sample channel 90, containing the reagent or sample fluid, is co-aligned with and moved into the fluid communication with the second dispensing port 37 of the dispensing conduit 35 and the upper communication port 46 of the primary passage 45. The dispensing actuator 22 is therefore fluidly coupled to the sample path 33 to fluidly dispense the reagent or sample fluid out of the nozzle member 48. Moreover, to isolate the aspiration actuator 21 from the sample path 33, the corresponding aspiration port 32 of the aspiration conduit 30 is dead-ended into the rotor face 51, and thereby out of fluid communication with the sample path (FIG. 18).

In this embodiment, thus, it will be appreciated that the dispensable volume of the sample path 33 is essentially the same as that of the sample channel 90. When the rotor element 52 rotates to the dispensing condition (FIGS. 16 and 18), only the sample or reagent fluid contained in the sample channel 90 is fluidly accessible to the dispensing actuator. It will be understood, however, that volumetric quantities less than the full volume of the sample channel 90 may be dispensed through precision operation of the dispensing actuator 22.

Figure 19:
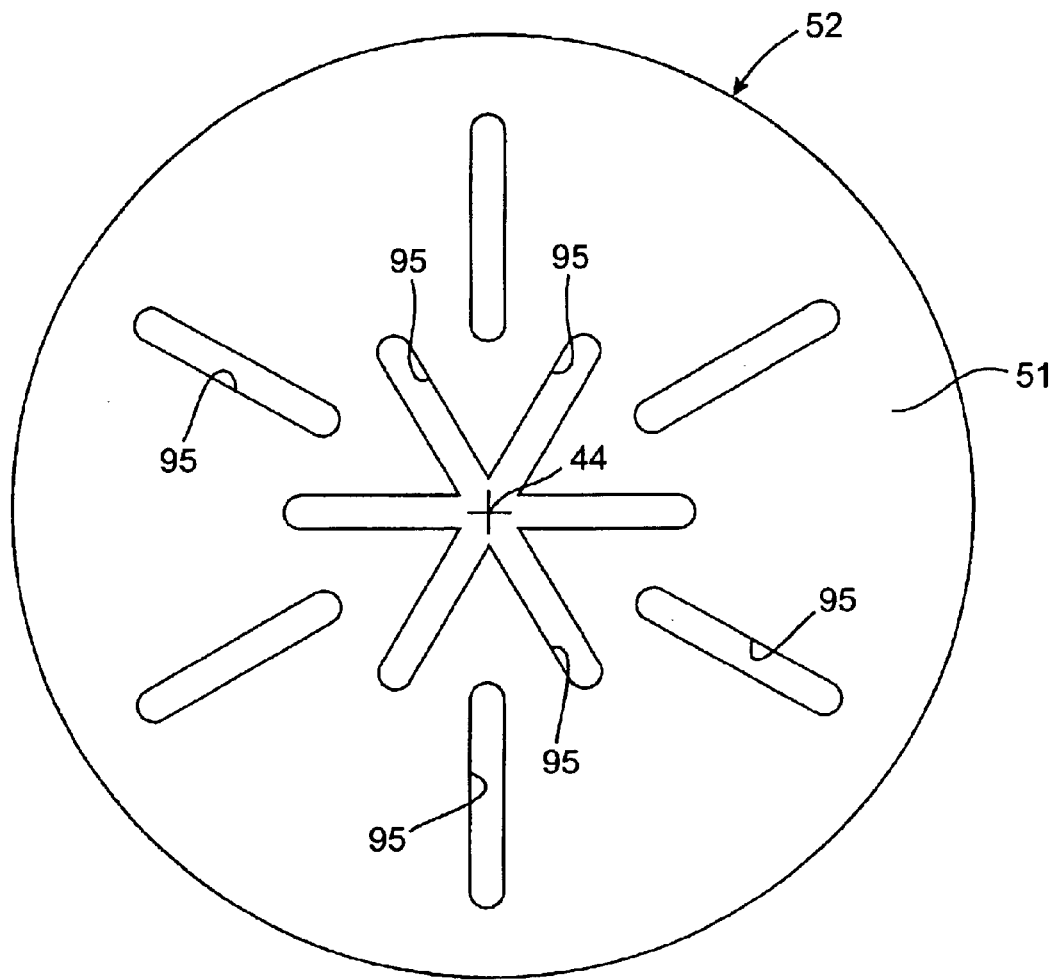
FIG. 19 is an enlarged, bottom plan view of the rotor face of the alternative embodiment rotor element

As best shown in FIG. 19, each sample channel 90 is slotted into the substantially planar rotor face 51 of the rotor element 52. Further, each equally spaced sample channel 90 is elongated in shape, and extends generally along a radial line intersecting the rotational axis 44 of the rotor face 51. Accordingly, at the rotor-stator interface (i.e., the high pressure sliding contact between the stator face 41 and the rotor face 51), the rotor element 52 either reciprocates or rotates in one direction clockwise or counter clockwise to orient the valve assembly in the aspiration condition or the dispensing condition.

These sample channels 90 preferably have a length in the range of about 1.0 mm to about 6.0 mm, and have a transverse cross-sectional area of about 0.3 $mm^2$ to about 1 $mm^2$. Accordingly, the volumetric capacity of the sample channel 90 is preferably in the range of about 0.5 $\mu l$ to about 2.0 $\mu l$. In comparison, the primary passage 45 and the nozzle passage 50 of the outlet preferably has a volume in the range of 0.1 $\mu l$ to about 2.0 $\mu l$.

The separation of the aspiration duty from the nozzle member 48 has several functional advantages. One benefit is that the total volume of sample is contained in the sample channel 90. Unused sample or reagent may be returned to the source, during dispense (FIG. 18) via the source path 23 significantly reducing sample and reagent waste volumes. An added benefit is that the nozzle member 48 may be greatly reduced in length to shorten the dispense path and pre-dispensing.

Another benefit of this design is that a spacing and order of the source reservoir array does not need to match that of the targeted test sites. That is, since the nozzle member 48 are not employed for both the aspiration and dispensing functions, the aspiration inlets (not shown), fluidly coupled to source conduits 87, can be set at one spacing and order (e.g., 96 well format), while the nozzle members 48 can be set to a different spacing and order (e.g., 1536 well format). Accordingly, the aspiration versatility is substantially increased. For example, some applications require individual manipulation of aspiration tips, such as applications that reformat individual positive samples to one destination plate from a multiplicity of positive and negative samples in a source plate.

In yet another advantage of this design, the transverse cross-sectional dimension of the aspiration and source conduits 30, 87, on the aspiration side, can be different from that of the dispensing conduits 35 and the primary passages 45 in the manifold device 28 and the nozzle passages 50 of the nozzle member 48, on the dispensing side. For example, it would be desirable to provide a large bore aspiration conduit 30 and source conduit 87 to facilitate rapid sample aspiration into the sample channel. In contrast, it would be desirable to provide a smaller bore for the nozzle passages 50 to facilitate ejection of smaller discrete volumes. Otherwise, when a smaller bore is utilized for restrictive flow of the dispense nozzle, in the previous embodiment, effective aspiration is compromised.

Lastly, the permissible wider cross-sectional dimension of the aspiration inlet allows for the inclusion of filtering devices. For example, by incorporating a filter on the inlet side, small particulates in the reagent or sample fluid that would normally clog, and render useless, a small bore nozzle can be removed. Such a filter could be exchangeable and would contain a high surface area allowing for filtering of particulates without frequent clogging. Typical of such filtering devices include frits commonly used in solid phase extraction or liquid chromatography devices.

Referring back to FIGS. 15 and 16, this embodiment of the present invention may further include a flush passage 91 in the manifold device 28 having an upper central flush port 92 terminating at the stator face 41, and an opposite end in fluid communication with a flush source 93. The central flush port 92 is aligned substantially co-axial with the rotational axis 44 of the rotor element 52 for continuous fluid communication with a flush channel 95 slotted in the rotor face 51 (FIG. 19).

Figure 15:
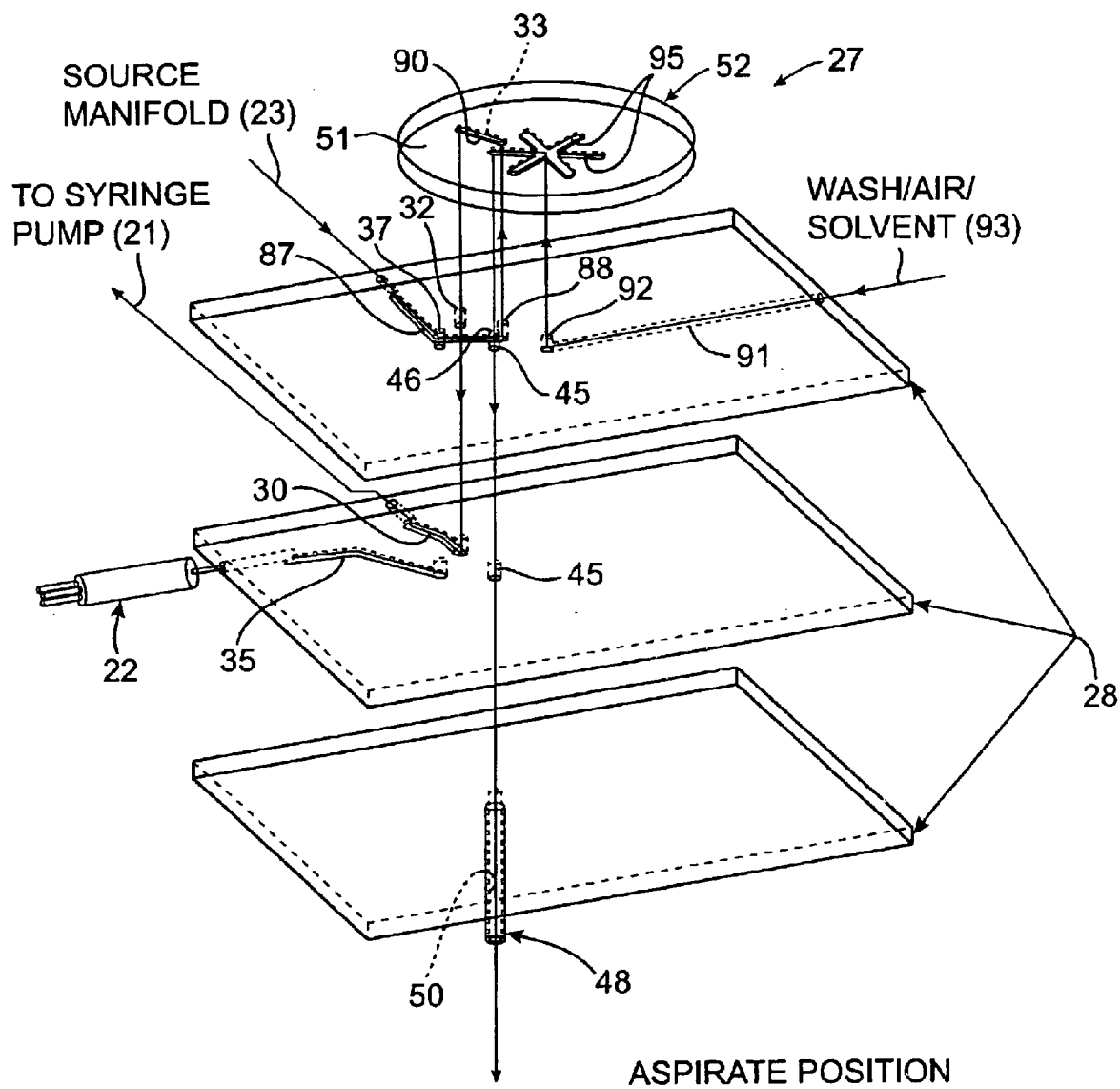
FIG. 15 is an exploded bottom perspective view of one fluid path of an alternative embodiment hybrid valve apparatus in the aspiration condition.

In the aspiration condition of FIGS. 15 and 17, this flush channel 95 in the rotor element 52 is fluidly couples the flush port 92 of the flush passage 91 to the upper communication port 46 of the corresponding primary passage 45. Thus, while the reagent or sample fluid is being aspirated into the corresponding sample path 33, the primary passages 45 and the nozzle passages 50 may be simultaneously flushed or cleaned with wash fluid or the like from the wash source 93. In contrast, when the rotor element is rotated to the dispensing condition of FIGS. 16 and 18, the flush channel 95 slotted in the rotor face fluidly couples the flush port 92 of the flush passage 91 to the upper communication opening 88 of the source conduit 87. Therefore, when the reagent or sample fluid is being dispensed from the sample path 33 through the corresponding nozzle member 48, unused sample or reagent could be returned to the source reservoir 23 and the aspirate path flushed.

Figure 20:
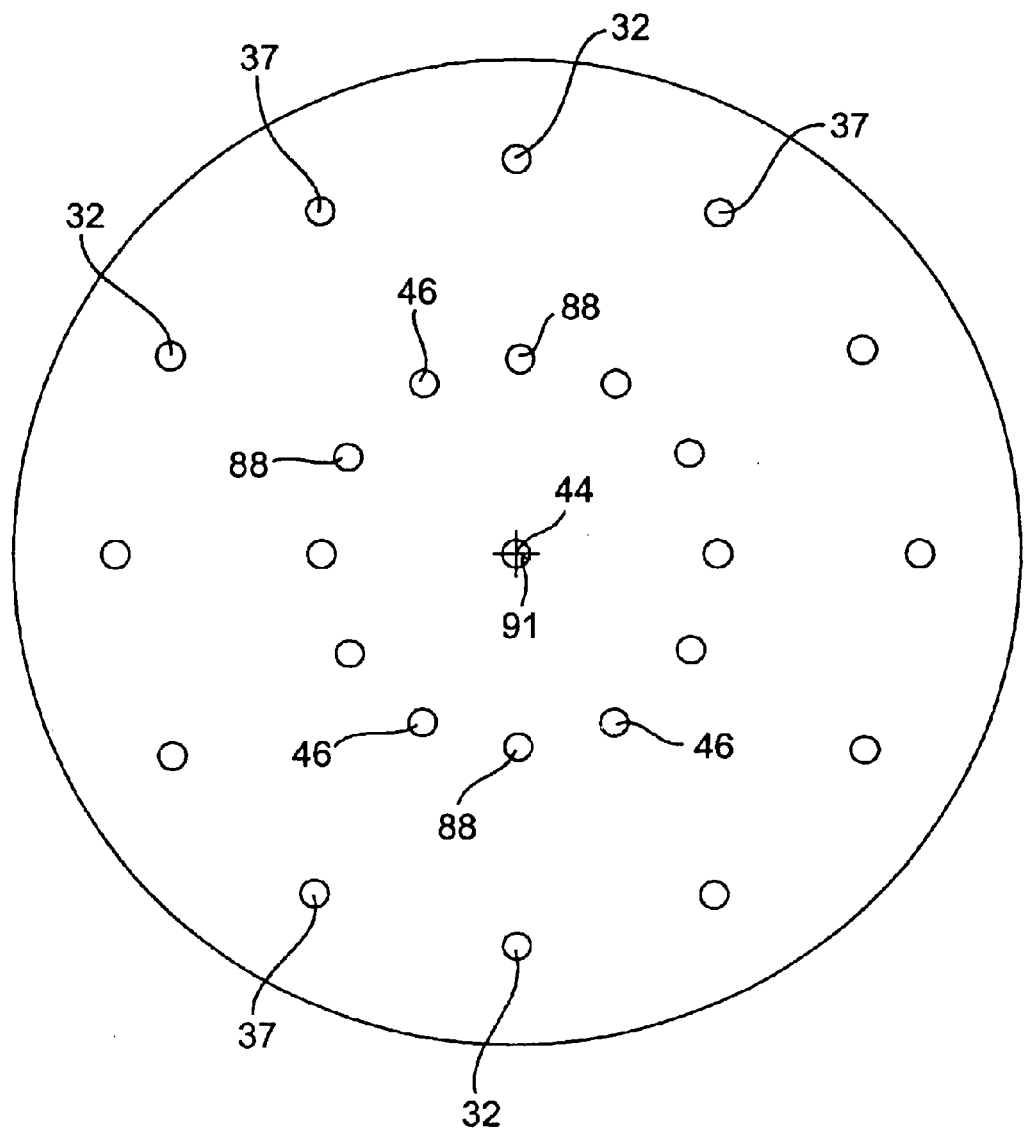
FIG. 20 is an enlarged, top plan view of the stator face of the stator element of the alternative embodiment rotor element.

Preferably, the flush channel 95 is provided by a plurality of equally spaced elongated slots which extend generally along a radial line intersecting the rotational axis 44 of the rotor face 51. These radially extending flush channels intersect at the rotational axis 44 so that the flush channels are in continuous fluid communication with the central flush port 92. As shown in FIG. 20, the upper communication ports 46 of the primary passages 45 and the upper communication openings 88 of the source conduits 87 are alternately spaced about the rotational axis 44. Accordingly, each rotation movement of the rotor is element 52 between the aspiration condition (FIGS. 15 and 17) and the dispensing condition (FIGS. 16 and 18) alternates fluid communication with the nozzle passages 50 and the source conduits 87.

Accordingly, at the rotor-stator interface (i.e., the high pressure sliding contact between the stator face 41 and the rotor face 51), the rotor element 52 either reciprocates or rotates in one direction clockwise or counter clockwise to orient the valve assembly in the aspiration condition or the dispensing condition.

Although only a few embodiments of the present inventions have been described in detail, it should be understood that the present inventions may be embodied in many other specific forms without departing from the spirit or scope of the inventions.

What is claimed is:

1. A hydraulic hybrid valve system to enable transfer of a liquid sample slug from a reservoir to a test site on a substrate surface comprising:

a valve assembly movable between an aspiration condition and a dispensing condition;

a communication structure having a dispensing orifice;

an aspiration actuator;

a dispensing actuator; and a distribution manifold device providing a liquid aspiration conduit containing a driving liquid and having a first aspiration port for liquid communication with the aspiration actuator, and a second aspiration port in selective liquid communication with the valve assembly to selectively aspirate a liquid sample slug from the reservoir through said dispensing orifice of said communication structure defining a discrete sample path containing said driving liquid and extending from the dispensing orifice and through at least a portion of said manifold device for liquid communication with said valve assembly, when the valve assembly is in the aspiration condition, said manifold device further providing a liquid dispensing conduit containing a driving liquid and having a first dispensing port for liquid communication with the dispensing actuator, and a second dispensing port in selective liquid communication with the valve assembly to selectively dispense at least one droplet of the liquid sample slug from said dispensing orifice of said communication structure when the valve assembly is in the dispensing condition, wherein, in the aspiration condition, said sample path is out of liquid communication with the dispensing actuator and, in the dispensing condition, said sample path is out of liquid communication with the aspiration actuator.

2. The hybrid valve system as defined by claim 1, wherein said through at least a portion of said manifold includes a primary passage portion of the sample path.

3. The hybrid valve system as defined by claim 2, wherein said communication structure includes a nozzle member terminating at a said dispensing orifice configured to aspirate said sample slug and dispense said droplet.

4. The hybrid valve system as defined by claim 3, wherein said primary passage portion is of a transverse cross-sectional area from about 0.2 mm$^2$ to about 0.8 mm$^2$.

5. The hybrid valve system as defined by claim 2, wherein said manifold device includes a stator face containing the second aspiration port and the second dispensing port, and said valve assembly includes a valve body having a contact face slideably contacting the stator face at a stator-contact interface for sliding sealed contact between the aspiration condition, fluidly coupling the second aspiration port to the primary passage portion of the sample path, and the dispensing condition, fluidly coupling the second dispensing port to the primary passage portion of the sample path.

6. The hybrid valve system as defined by claim 5, wherein said contact face of the valve body includes an aspiration channel, fluidly coupling the second aspiration port to the primary passage portion of the sample path through the aspiration channel, in the aspiration condition, and a dispensing channel, fluidly coupling the second dispensing port to the primary passage portion of the sample path through the dispensing channel, in the dispensing condition.

7. The hybrid valve system as defined by claim 6, wherein
said primary passage portion of the sample path includes an upper communication port terminating at the stator face for liquid communication with the aspiration channel in the aspiration condition, and for liquid communication with the dispensing channel in the dispensing condition.

8. The hybrid valve apparatus system as defined by claim 7, wherein
said communication structure includes a nozzle member terminating at said dispensing orifice to aspirate said sample slug and dispense said droplet.

9. The hybrid valve system as defined by claim 6, wherein
at least one of said valve body and said manifold device is rotatable about a rotation axis extending substantially perpendicular to the stator-contact interface to rotate said contact face, said aspiration channel and said dispensing channel relative to the stator face between the aspiration condition and the dispensing condition.

10. The hybrid valve system as defined by claim 9, wherein
said dispensing channel and said aspiration channel extend in a direction substantially radially about said rotational axis.

11. The hybrid valve system as defined by claim 1, further including:
a digitally regulated hydraulic pressure system for liquid communication with the dispensing actuator for precision operation thereof.

12. The hybrid valve assembly as defined by claim 3, wherein
said nozzle member having one end mounted to said manifold device and fluidly coupled to said primary passage portion.

13. The hybrid valve assembly as defined by claim 1, wherein
said manifold device includes a first connection region configured to enable connection of the aspiration actuator directly to the manifold device at the first aspiration port.

14. The hybrid valve assembly as defined by claim 13, wherein
said manifold device includes a second connection region configured to enable connection of the dispensing actuator directly to the manifold device at the first dispensing port.

15. A method of transferring a liquid sample from a liquid sample reservoir to a test site on a target substrate comprising:
providing a liquid distribution manifold device defining a liquid aspiration conduit containing a driving liquid and having a first aspiration port for liquid communication with an aspiration actuator and a second aspiration port in liquid communication with a valve assembly, said manifold device further defining a liquid dispensing conduit containing a driving liquid and having a first dispensing port for liquid communication with a dispensing actuator and a second dispensing port in liquid communication with the valve assembly;
positioning the valve assembly in an aspiration condition, fluidly coupling the aspiration actuator to a discrete sample path extending from a dispensing orifice and through at least a primary passage portion of said manifold device for liquid communication with said valve assembly, and fluidly decoupling the dispensing actuator from the sample path;
in said aspiration condition, actuating the aspiration actuator to aspirate a liquid sample slug from a said sample reservoir into the sample path through said dispensing orifice;
positioning the valve assembly in a dispensing condition, fluidly coupling the dispensing actuator to the sample path, and fluidly decoupling the aspiration actuator from the same path; and
in said dispensing condition, actuating the dispensing actuator to dispense at least one droplet of the liquid sample slug out of said sample path through said dispensing orifice.

16. The method according to claim 15, wherein
said primary passage portion of said manifold device having a upper communication port terminating at a stator face of the manifold, said stator face further containing the second aspiration port and the second dispensing port.

17. The method according to claim 16, wherein
said positioning the valve assembly to the aspiration condition or the dispensing condition includes slideably engaging a contact face of the valve assembly against the stator face of the manifold device at a stator-contact interface, to fluidly couple the aspiration actuator to the primary passage portion of the sample path or fluidly couple the dispensing actuator to the primary passage portion of the sample path, respectively.

18. The method according to claim 17, wherein
said slideably engaging includes rotating an aspiration channel and a dispensing channel in the contact face of the valve assembly about a rotation axis thereof, relative the stator face, to
fluidly couple the upper communication port with the second aspiration port, through the aspiration channel, in the aspiration condition, and
fluidly couple the upper communication port with the second dispensing port, through the dispensing channel, in the dispensing condition.

19. The method according to claim 15, wherein
said primary passage portion having a transverse cross-sectional area from about 0.2 mm$^2$ to about 0.8 mm$^2$.

20. The method according to claim 15, further including:
digitally regulated the hydraulic pressure of the dispensing actuator for precision operation thereof.

21. A hybrid valve system to enable transfer of a liquid sample slug from a reservoir to a test site on a substrate surface comprising:
a valve assembly movable between an aspiration condition and a dispensing condition;
an aspiration actuator;
a dispensing actuator; and
a manifold providing a fluid aspiration conduit having a first aspiration port for fluid communication with the aspiration actuator, and a second aspiration port in selective fluid communication with the valve assembly to selectively aspirate the liquid sample slug from the reservoir into a discrete sample path, a primary passage portion thereof that extends through at least a portion of said manifold for fluid communication with said valve assembly, when the valve assembly is in the aspiration condition, said primary passage portion having a transverse cross-sectional area from about 0.2 mm² to about 0.8 mm², said manifold further providing a fluid dispensing conduit having a first dispensing port for fluid communication with the dispensing actuator, and a second dispensing port in selective fluid communication with the valve assembly to selectively dispense at least one droplet of the liquid sample slug from the sample path when the valve assembly is in the dispensing condition, wherein, in the aspiration condition, said sample path is out of fluid communication with the dispensing actuator and, in the dispensing condition, said sample path is out of fluid communication with the aspiration actuator.

22. The hybrid valve system as defined by claim 21, further including:
  a nozzle member having one end fluidly coupled to said primary passage portion and an opposite end terminating at a dispensing orifice configured to dispense said droplet.

23. The hybrid valve system as defined by claim 22, wherein
  the one end of said nozzle member being mounted to said manifold and fluidly coupled to said primary passage portion.

24. The hybrid valve system as defined by claim 21, wherein
  said manifold includes a first connection region configured to enable connection of the aspiration actuator directly to the manifold at the first aspiration port.

25. The hybrid valve system as defined by claim 21, wherein
  said manifold includes a second connection region configured to enable connection of the dispensing actuator directly to the manifold at the first dispensing port.

26. The hybrid valve system as defined by claim 21, wherein
  said manifold includes a stator face containing the second aspiration port and the second dispensing port, and said valve assembly includes a valve body having a contact face slideably contacting the stator face at a stator-contact interface for sliding sealed contact between
    the aspiration condition, fluidly coupling the second aspiration port to the primary passage portion of the sample path, and
    the dispensing condition, fluidly coupling the second dispensing port to the primary passage portion of the sample path.

27. The hybrid valve system as defined by claim 26, wherein
  said contact face of the valve body includes
    an aspiration channel, fluidly coupling the second aspiration port to the primary passage portion of the sample path through the aspiration channel, in the aspiration condition, and
    a dispensing channel, fluidly coupling the second dispensing port to the primary passage portion of the sample path through the dispensing channel, in the dispensing condition.

28. The hybrid valve system as defined by claim 27, wherein
  said manifold includes a primary passage defining at least a portion of the sample path, and having an upper communication port terminating at the stator face for fluid communication with the aspiration channel in the aspiration condition, and for fluid communication with the dispensing channel in the dispensing condition.

29. The hybrid valve system as defined by claim 28, further including:
  a nozzle member having one end fluidly coupled to said primary passage and an opposite end terminating at a dispensing orifice configured to dispense said droplet.

30. The hybrid valve apparatus as defined by claim 27, wherein
  at least one of said valve body and said manifold is rotatable about a rotation axis extending substantially perpendicular to the stator-contact interface to rotate said contact face, said aspiration channel and said dispensing channel relative to the stator face between the aspiration condition and the dispensing condition.

31. The hybrid valve system as defined by claim 30, wherein
  said dispensing channel and said aspiration channel extend in a direction substantially radially about said rotational axis.

32. The hybrid valve system as defined by claim 21, further including:
  a digitally regulated hydraulic pressure system for fluid communication with the dispensing actuator for precision operation thereof.

33. A hybrid valve system to enable transfer of a liquid sample slug from a reservoir to a test site on a substrate surface comprising:
  an aspiration actuator;
  a dispensing actuator; and
  a digitally regulated hydraulic pressure system in fluid communication with the dispensing actuator for precision operation thereof;
  a valve assembly movable between an aspiration condition and a dispensing condition;
  a manifold providing a fluid aspiration conduit having a first aspiration port for fluid communication with the aspiration actuator, and a second aspiration port in selective fluid communication with the valve assembly to selectively aspirate the liquid sample slug from the reservoir into a discrete sample path, a primary passage portion thereof that extends through at least a portion of said manifold for fluid communication with said valve assembly, when the valve assembly is in the aspiration condition, said manifold device further providing a fluid dispensing conduit having a first dispensing port for fluid communication with the dispensing actuator, and a second dispensing port in selective fluid communication with the valve assembly to selectively dispense at least one droplet of the liquid sample slug from the sample path when the valve assembly is in the dispensing condition,
  wherein, in the aspiration condition, said sample path is out of fluid communication with the dispensing actuator and, in the dispensing condition, said sample path is out of fluid communication with the aspiration actuator.

34. The hybrid valve system as defined by claim 33, further including:
  a nozzle member having one end fluidly coupled to said primary passage portion and an opposite end terminating at a dispensing orifice configured to dispense said droplet.

35. The hybrid valve system as defined by claim 34, wherein
  the one end of said nozzle member being mounted to said manifold and fluidly coupled to said primary passage portion.

36. The hybrid valve system as defined by claim 33, wherein said manifold includes a first connection region configured to enable connection of the aspiration actuator directly to the manifold at the first aspiration port.

37. The hybrid valve system as defined by claim 33, wherein said manifold includes a second connection region configured to enable connection of the dispensing actuator directly to the manifold at the first dispensing port.

38. The hybrid valve system as defined by claim 33, wherein said manifold includes a stator face containing the second aspiration port and the second dispensing port, and said valve system includes a valve body having a contact face slideably contacting the stator face at a stator-contact interface for sliding sealed contact between the aspiration condition, fluidly coupling the second aspiration port to the primary passage portion of the sample path, and the dispensing condition, fluidly coupling the second dispensing port to the primary passage portion of the sample path.

39. The hybrid valve system as defined by claim 38, wherein said contact face of the valve body includes an aspiration channel, fluidly coupling the second aspiration port to the primary passage portion of the sample path through the aspiration channel, in the aspiration condition, and a dispensing channel, fluidly coupling the second dispensing port to the primary passage portion of the sample path through the dispensing channel, in the dispensing condition.

40. The hybrid valve system as defined by claim 39, wherein said manifold includes a primary passage defining at least a portion of the sample path, and having an upper communication port terminating at the stator face for fluid communication with the aspiration channel in the aspiration condition, and for fluid communication with the dispensing channel in the dispensing condition.

41. The hybrid valve system as defined by claim 40, further including:

a nozzle member having one end fluidly coupled to said primary passage and an opposite end terminating at a dispensing orifice configured to dispense said droplet.

42. The hybrid valve system as defined by claim 39, wherein at least one of said valve body and said manifold is rotatable about a rotation axis extending substantially perpendicular to the stator-contact interface to rotate said contact face, said aspiration channel and said dispensing channel relative to the stator face between the aspiration condition and the dispensing condition.

43. The hybrid valve system as defined by claim 42, wherein said dispensing channel and said aspiration channel extend in a direction substantially radially about said rotational axis.

\* \* \* \* \*

UNITED STATES PATENT AND TRADEMARK OFFICE
CERTIFICATE OF CORRECTION

PATENT NO.        : 6,852,291 B1
APPLICATION NO. : 09/689548
DATED             : February 8, 2005
INVENTOR(S)       : Johnson et al.

Page 1 of 1

It is certified that error appears in the above-identified patent and that said Letters Patent is hereby corrected as shown below:

Col. 13, line 11,    change "corresponding is dispensing" to --corresponding dispensing--.

Col. 17, line 10 (Claim 8),    change "valve apparatus system" to --valve system--.

Col. 18, line 5 (Claim 15),    change "slug from a said" to --slug from said--.

Signed and Sealed this

Twenty-fourth Day of November, 2009

David J. Kappos
*Director of the United States Patent and Trademark Office*